(12) United States Patent
Givens et al.

(10) Patent No.: US 8,777,869 B2
(45) Date of Patent: *Jul. 15, 2014

(54) SYSTEMS, METHODS AND PRODUCTS FOR DIAGNOSTIC HEARING ASSESSMENTS DISTRIBUTED VIA THE USE OF A COMPUTER NETWORK

(75) Inventors: Gregg D. Givens, Greenville, NC (US); David C. Balch, Greenville, NC (US); Timothy Murphy, Greenville, NC (US); Adrian Blanarovich, Greenville, NC (US); Patrick Keller, Jacksonville, NC (US)

(73) Assignee: East Carolina University, Greenville, NC (US)

( * ) Notice: Subject to any disclaimer, the term of this patent is extended or adjusted under 35 U.S.C. 154(b) by 23 days.

This patent is subject to a terminal disclaimer.

(21) Appl. No.: 13/610,190

(22) Filed: Sep. 11, 2012

(65) Prior Publication Data

US 2013/0006140 A1      Jan. 3, 2013

Related U.S. Application Data

(60) Division of application No. 12/944,368, filed on Nov. 11, 2010, now Pat. No. 8,287,462, which is a (Continued)

(51) Int. Cl.
*A61B 5/00* (2006.01)
*A61B 5/12* (2006.01)
*G06F 19/00* (2011.01)
*G06Q 50/22* (2012.01)

(52) U.S. Cl.
CPC .................. *A61B 5/121* (2013.01); *A61B 5/123* (2013.01); *A61B 5/125* (2013.01); *A61B 5/12* (2013.01); *G06F 19/3418* (2013.01); *G06Q 50/22* (2013.01)
USPC ........................................................ 600/559

(58) Field of Classification Search
CPC ........ A61B 5/121; A61B 5/123; A61B 5/125; A61B 5/12; G06F 19/3418; G06Q 50/22
USPC ............. 600/559, 300, 301; 607/116; 73/645, 73/585; 707/8, 10, 100; 709/203, 232; 718/102, 108; 702/19, 54, 76, 108, 702/122, 124, 183; 381/23.1
See application file for complete search history.

(56) References Cited

U.S. PATENT DOCUMENTS 3,392,241 A    7/1968   Weiss et al.
3,536,835 A    10/1970  Rawls et al.

(Continued)

FOREIGN PATENT DOCUMENTS

WO    WO98/02083    1/1998
WO    WO99/04043    1/1999
WO    WO01/06916    2/2001

OTHER PUBLICATIONS

Frank, Ansi Update: Specification of Audiometers, Nov. 1997, American Journal of Audiology, vol. 6, No. 3, pp. 29-32.

(Continued)

*Primary Examiner* — Brian Szmal
(74) *Attorney, Agent, or Firm* — Myers Bigel Sibley & Sajovec, P.A.

(57) ABSTRACT

The systems, methods and associated devices performing diagnostic hearing tests which use a computer network to allow interaction between a test administration site and one or a plurality of remote patient sites. The test can be administered by an audiologist or clinician at a site remote from the patient, in a manner, which can allow interaction between the user and the clinician during at least a portion of the administration of the test. The diagnostic hearing tests can be performed such that they meet standardized guidelines such as ANSI requirements or certification standards and can include distortion product emission level measurements or middle ear compliance measurements.

20 Claims, 17 Drawing Sheets

Related U.S. Application Data continuation of application No. 12/256,096, filed on Oct. 22, 2008, now Pat. No. 7,854,704, which is a continuation of application No. 11/113,560, filed on Apr. 25, 2005, now Pat. No. 7,530,957, which is a division of application No. 10/068,016, filed on Feb. 5, 2002, now Pat. No. 6,916,291.

(60) Provisional application No. 60/266,988, filed on Feb. 7, 2001, provisional application No. 60/295,640, filed on Jun. 4, 2001.

(56) References Cited

U.S. PATENT DOCUMENTS

| | | |
|---|---|---|
| 3,793,484 A | 2/1974 | Feezor |
| 3,793,485 A | 2/1974 | Feezor et al. |
| 3,799,146 A | 3/1974 | John et al. |
| 3,808,354 A | 4/1974 | Feezor et al. |
| 3,974,335 A | 8/1976 | Blackledge |
| 4,002,161 A | 1/1977 | Klar et al. |
| 4,009,707 A | 3/1977 | Ward |
| 4,024,499 A | 5/1977 | Bosscher |
| 4,038,496 A | 7/1977 | Feezor |
| 4,201,225 A | 5/1980 | Bethea, III et al. |
| 4,275,744 A | 6/1981 | Thornton et al. |
| 4,284,847 A | 8/1981 | Besserman |
| 4,374,526 A | 2/1983 | Kemp |
| 4,388,595 A | 6/1983 | Brooks |
| 4,489,610 A | 12/1984 | Slavin |
| 4,556,069 A | 12/1985 | Dalton, Jr. et al. |
| 4,601,295 A | 7/1986 | Teele |
| 4,688,582 A | 8/1987 | Heller et al. |
| 4,759,070 A | 7/1988 | Voroba et al. |
| 4,768,165 A | 8/1988 | Hohn |
| 4,847,763 A | 7/1989 | Moser et al. |
| 4,884,447 A | 12/1989 | Kemp et al. |
| 4,961,895 A | 10/1990 | Klein |
| 5,105,822 A | 4/1992 | Stevens et al. |
| 5,197,332 A | 3/1993 | Shennib |
| 5,216,425 A | 6/1993 | Erhage |
| 5,303,327 A | 4/1994 | Sturner et al. |
| 5,372,142 A | 12/1994 | Madsen et al. |
| 5,402,493 A | 3/1995 | Goldstein |
| 5,419,312 A | 5/1995 | Arenberg et al. |
| 5,421,818 A | 6/1995 | Arenberg |
| 5,428,998 A | 7/1995 | Downs |
| 5,441,047 A | 8/1995 | David et al. |
| 5,473,460 A | 12/1995 | Haner et al. |
| 5,474,529 A | 12/1995 | Arenberg |
| 5,476,446 A | 12/1995 | Arenburg |
| 5,526,819 A | 6/1996 | Lonsbury-Martin et al. |
| 5,546,956 A | 8/1996 | Thornton |
| 5,594,174 A | 1/1997 | Keefe |
| 5,628,330 A | 5/1997 | Upham |
| 5,651,371 A | 7/1997 | Keefe |
| 5,664,577 A | 9/1997 | Lonsbury-Martin et al. |
| 5,687,717 A | 11/1997 | Halpern et al. |
| 5,697,379 A | 12/1997 | Neely et al. |
| 5,699,809 A | 12/1997 | Combs et al. |
| 5,734,827 A | 3/1998 | Thornton et al. |
| 5,755,230 A | 5/1998 | Schmidt et al. |
| 5,776,144 A | 7/1998 | Leysieffer et al. |
| 5,776,179 A | 7/1998 | Ren et al. |
| 5,792,072 A | 8/1998 | Keefe |
| 5,792,073 A | 8/1998 | Keefe |
| 5,811,681 A | 9/1998 | Braun et al. |
| 5,825,894 A | 10/1998 | Shennib |
| 5,868,682 A | 2/1999 | Combs et al. |
| 5,885,225 A | 3/1999 | Keefe et al. |
| 5,917,375 A | 6/1999 | Lisco et al. |
| 5,928,160 A | 7/1999 | Clark et al. |
| 5,954,667 A | 9/1999 | Finkenzeller et al. |
| 6,033,076 A | 3/2000 | Bracuning et al. |
| 6,051,849 A | 4/2000 | Davis et al. |
| 6,071,246 A | 6/2000 | Stürzebecher et al. |
| 6,083,156 A | 7/2000 | Lisiecki |
| 6,086,541 A | 7/2000 | Rho |
| 6,110,126 A | 8/2000 | Zoth et al. |
| 6,171,237 B1 | 1/2001 | Avitall et al. |
| 6,283,761 B1 | 9/2001 | Joao |
| 6,319,207 B1 | 11/2001 | Naidoo |
| 6,322,521 B1 | 11/2001 | Hou |
| 6,350,243 B1 | 2/2002 | Johnson |
| 6,366,863 B1 | 4/2002 | Bye et al. |
| 6,379,314 B1 | 4/2002 | Horn |
| 6,428,485 B1 | 8/2002 | Rho |
| 6,468,224 B1 | 10/2002 | Foreman et al. |
| 6,513,060 B1 | 1/2003 | Nixon et al. |
| 6,535,878 B1 | 3/2003 | Guedalia et al. |
| 6,647,345 B2 | 11/2003 | Bye et al. |
| 6,916,291 B2 | 7/2005 | Givens et al. |
| 6,917,373 B2 | 7/2005 | Vong et al. |
| 6,974,421 B1 | 12/2005 | Causevic et al. |
| 7,016,504 B1 | 3/2006 | Shennib |
| 7,530,957 B2 | 5/2009 | Givens et al. |
| 7,854,704 B2 | 12/2010 | Givens et al. |
| 8,287,462 B2 * | 10/2012 | Givens et al. ............. 600/559 |
| 2001/0027335 A1 | 10/2001 | Meyerson et al. |
| 2002/0076056 A1 | 6/2002 | Pavlakos |
| 2002/0124100 A1 | 9/2002 | Adams |

OTHER PUBLICATIONS

*Hearing Screening with the OtoScreen I, General Information*: http://www.handtronix.com/HTX/OTOInfo.html, 3 pages, (printed Sep. 6, 2000).

*What's new in hearing screening and audiology*, http://www.handtronix.com, 4 pages (date of publication Feb. 2001), (printed Apr. 19, 2002).

Alsarraf et al., *Otitis Media Health Status Evaluation: A Pilot Study for the Investigation of Cost-Effective Outcomes of Recurrent Acute Otitis Media Treatment*, Annals of Otology, Rhinology and Laryngology 107(2): 120-128, (1998).

Alusi et al., *Tele-education: the virtual medical laboratory*, J Telemed Telecare 3(Suppl 1): 79-81, Abstract Only, 1 page, (1997).

American Academy of Pediatrics, *Newborn and Infant Hearing Loss: Detection and Intervention*, Pediatrics 103(2): 527-530, (1999).

Bess et al., *Children with Minimal Sensorineural Hearing Loss: Prevalence, Educational Performance and Functional Status*, Ear and Hearing 19 (5): 339-354, (1998).

Blakeslee et al., *Practice of otolaryngology via telemedicine*, Laryngoscope 108(1) Pt 1:1-7, Abstract Only, 1 sheet, (Jan. 1998).

Burgess et al., *Abstract of Overview of telemedicine applications for otolaryngology*, Jnl Laryngoscope, 109(9): 1433-1437, (Sep. 1999).

Carrell et al., *Letter to the Editor Interactive Software for Evaluating Auditory Discrimination*, Ear & Hearing, pp. 175-176, (1999).

Collins, J., *Prevalence of Selected Chronic Conditions*, U.S. 1990-1992, Natl Center for Health Statistics, Vital Health Statistics, 10(194): iii-8, (1997).

Crump et al., *A field trial of the NASA Telemedicine Instrument Pack in a family practice*, Aviat Space Environ Med 67(11): 1080-1085, Abstract Only, 1 page, (Nov. 1996).

Finitzo et al.., *The Newborn with Hearing Loss: Detection in the Nursery*, Pediatrics (102): 1452-1460, (1998).

Freid et al., *Ambulatory Health Care Visits by Children: Principal Diagnosis and Place of Visit*, Natl Center for Health Statistics, Vital and Health Statistics 13(137): 17, iii-23, (1998).

Furukawa et al., *Telemedicine in laryngology*, Jibi Inkoka Tokeibu Geka 70(12): 855-856, Abstract Only, 1 page, (1998).

Givens et al., *Internet Application to Tele-Audiology-"Nothin' but Net"*, Journal of Speech, Language, and Hearing Research, vol. 12 (2): 59-65, (Dec. 2003).

Givens et al., *Internet Based Tele-Audiometry System for the Assessment of Hearing: A Pilot Study*, Telemedicine Journal and e-Health, vol. 9 (4): 375-378, (2003).

Gorlin et al., *Hereditary Hearing Loss and Its Syndromes*, New York: Oxford University Press, p. xv-xxxiii, (1995).

Hall, J, W., *Handbook of Otoacoustic Emissions*, Singular Publishing Group, pp. 20 and 24 (1999).

(56) References Cited

OTHER PUBLICATIONS

Heneghan et al., *Telemedicine applications in otolaryngology*, IEEE Eng Med Biol Mag 18(4): 53-62, Abstract Only, 2 pages, (Jul.-Aug. 1999).

Holtan, Amy, *Patient reactions to specialist telemedicine consultations—a sociological approach*, J. Telemed Telecare 4: 206-213, (1998).

Hutchinson, J. R., *Telemedicine in otolaryngology*, Otolaryngol Clin North Am, 31(2): 319-329, Abstract, 1 page, (Apr. 1998).

Joint Committee on Infant Hearing Screening, 1994 Position Statement, American Speech-Language-Hearing Assn. 36(12), 11 pages, (Dec. 1994).

Kelly, L., *Using Silent Motion Pictures to Teach Complex Syntax to Adult Deaf Readers*, Journal of Deaf Studies and Deaf Education 3: 217-230, Abstract Only, 1 page, (1998).

Made et al., *Tele-otolaryngology consultations between two rural primary-care centres in southern Lapland and the University Hospital of Umeå*, J. Telemed Telecare 5, Suppl 1, S1:93-S1:94, (1999).

Martin, F.N., *A Study Guide Introduction to Audiology*, $2^{nd}$ Edition, University of Texas, 2 pages, (1991).

Masterson et al., *New & Emerging Technologies. Going Where We've Never Gone Before*, ASHA 41(3): 16-20 (May-Jun. 1999).

Morton, N,E., *Genetic Epidemiology of Hearing Impairment*, Annals of the New York Academy of Sciences 630: 16-31, (1991).

Natl Institute on Deafness and Other Communication Disorders, *Natl Strategic Research Plan: Hearing and Hearing Impairment*, Bethesda, MD, U.S. Dept. of Health and Human Services, Natl Institutes of Health, pp, ii-110, (1996).

Niskar et al., *Prevalence of Hearing Loss Among Children 6 to 19 Years of Age, The Third Natl Health and Nutrition Examination Survey*, Journal of the American Medical Assn, 279(14): 1071-1075, Abstract Only, 2 pages, (1998).

Schappert, *Office Visits for Otitis Media: United States, 1975-1990*, Advance Data 214: 1-20, (1992).

Steinberg, A., *Issues in Providing Mental Health Services to Hearing Impaired Persons*, Hospital & Community Psychiatry 42(4): 380-389, (1991).

Stern et al., *Telemedicine applications in otolaryngology*, Journal of Telemed Telecare 4 (Suppl 1): 74-75, (1998).

Straub, K., *Health care videoconferencing options cover wide range of applications, prices, quality*, Health Mgmt Tech 18(5): 52-3, 55-6, Abstract Only, 1 page, (Apr. 1997).

Wolbransky et al., *ATA Conference Report. Telemedicine in the new millennium*, MD Computing 16(4): 40-43, (Jul.-Aug. 1999).

Yoo et al, *Cochlear Modeling and Visualization on the Internet*, Int'l Congress Series No. 1191:1044-1045, (1999).

Yoshinaga-Itano et al., *Identification of Hearing Loss after age 18 Months is not Early Enough*, American Annals of the Deaf 143(5): 380-387, (1998).

Yoshinaga-Itano et al., *Language of Early and Later-Identified Children with Hearing Loss*, Pediatrics 102(5): 1161-1171, (1998).

Wilson et al., *Eastern North Carolina Health Care Atlas, A resource for healthier communities*, pp. ii-II.B.46, (1997).

\* cited by examiner

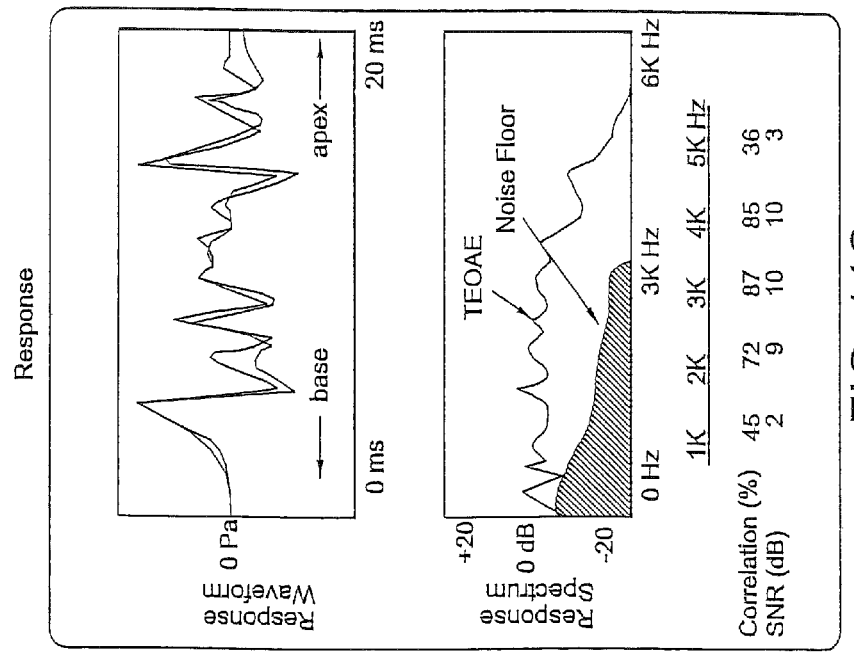
FIG. 14C.
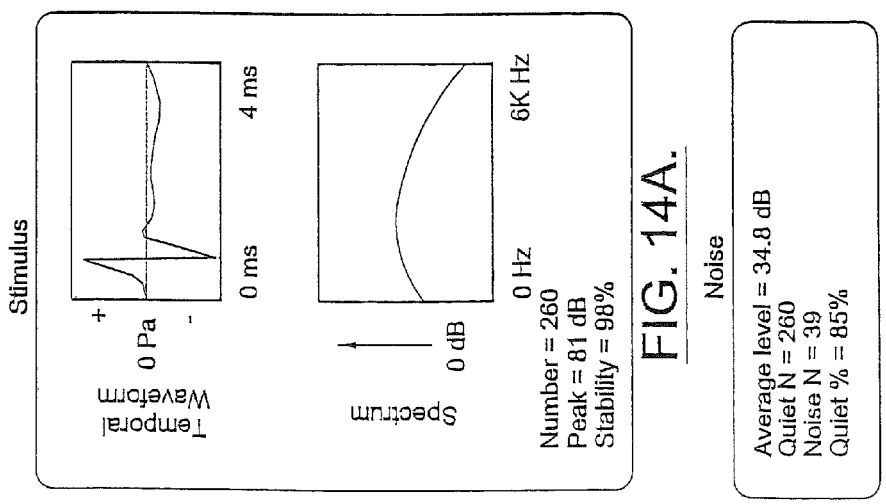
FIG. 14A.
FIG. 14B.

SYSTEMS, METHODS AND PRODUCTS FOR DIAGNOSTIC HEARING ASSESSMENTS DISTRIBUTED VIA THE USE OF A COMPUTER NETWORK

RELATED APPLICATIONS

This application is a continuation of U.S. patent application Ser. No. 12/944,368, filed Nov. 11, 2010, which is a continuation of U.S. patent application Ser. No. 12/256,096 filed Oct. 22, 2008, now U.S. Pat. No. 7,854,704, which is a continuation of U.S. patent application Ser. No. 11/113,560 filed Apr. 25, 2005, which issued on May 12, 2009 as U.S. Pat. No. 7,530,957, which is a divisional of U.S. patent application Ser. No. 10/068,016 filed Feb. 5, 2002, which issued as U.S. Pat. No. 6,916,291 on Jul. 12, 2005, which claims the benefit of priority of U.S. Provisional Application Ser. No. 60/266,988, filed Feb. 7, 2001, and U.S. Provisional Application Ser. No. 60/295,640, filed Jun. 4, 2001, the contents of which are hereby incorporated by reference as if recited in full herein.

FIELD OF THE INVENTION

The invention relates to hearing evaluation systems used to diagnose hearing impairments.

BACKGROUND OF THE INVENTION

It is estimated that approximately 28 million people, including 1.46 million children, have a hearing deficiency. Early identification of hearing loss and appropriate intervention can be critical to preventing or ameliorating further hearing loss or language delay or disorder. Indeed, early identification can be particularly important in children who are, typically, more receptive to rehabilitation.

Conventional hearing evaluation or assessment tests are performed in a clinical setting with personal interaction between the patient and a clinician. In these settings, the patient is often required to sit in a sound isolation booth and to visually signal to the clinician when sounds generated from an audiometer become audible. Unfortunately, this clinic or office setting structure can be burdensome and time consuming, particularly for those individuals located in remote or rural regions where health care options may be limited or in industrial settings where frequent or periodical screenings may be beneficial.

One presently operating website attempts to reach a broader audience by providing a hearing screening procedure over the Internet. The screening is available at the Universal Resource Locator (URL) "www.handtronix.com." This website provides a rough hearing screening which purports to indicate, as a result of the procedure, whether the user should obtain a diagnostic hearing test (apparently based on whether the user fails to discern one or more of the three or four tones provided during the test at particular volumes). For example, a sound at a frequency of about 1000 Hz may be generated from a personal computer, which is output to the user by the speakers at a certain volume. The sound frequency may then change to one of three other selected frequencies (such as 500 Hz, 2000 Hz, and 4000 Hz). The user can adjust the speaker volume until they can audibly detect the sound at that frequency. The results of such a screening are an indication of whether the user should seek a full hearing diagnostic evaluation. Unfortunately, this screening is not a diagnostic hearing test and does not meet ANSI guidelines.

In addition, recently, telemedicine has become a viable option for certain medical procedures. PCT/US98/13681 proposes an automated process for test tracking analysis and reporting of various diseases and tests. This document briefly notes that the automated system may be useful for administering non-invasive tests such as hearing tests in the home without the physical presence of a physician or audiologist. For these tests, this reference proposes a test kit which can be obtained from a retailer or organization which can include an electronic auditory (hearing) test which can be transmitted by an auditory transmitter such as telephone, modem, cable, computer network, television, radio, etc. As described, the patient inputs test answers into an inputting device, which can be similar to the auditory transmitter, which then directs the data into a data processing system which analyzes the data. The analysis can then generate an electronic diagnosis and forward the recommendation or diagnosis to the patient or to a physician or audiologist. Unfortunately, this proposed system automatically performs the test and does not employ an audiologist, clinician, or physician, during administration of the test. Further, this system does not describe the test itself, nor how to generate a reliable remotely administered test, which meets standardized ANSI based diagnostic hearing test requirements.

SUMMARY OF THE INVENTION

Embodiments of the present invention provide systems, methods and associated devices and computer program products for performing diagnostic hearing tests which use a computer network to allow interaction between a test administration site and one or more remote patient sites. The test can be administered by an audiologist or clinician at a site remote from the patient, in a manner which can allow interaction between the user and the clinician during at least a portion of the administration of the test. The diagnostic hearing tests can be performed such that they meet standardized guidelines such as ANSI requirements or regulatory or certification standards.

The computer network can be a local area network, a wide area network, an intranet (computers connected within a particular organization, company, coalition, or group) or can be the Internet (such as a global computer network, e.g., the world wide web). The hearing test can be performed such that the hearing tones (frequency and decibel level) are generated locally to the patient in response to commands selecting the desired tone/level which are transmitted from the expert or test administration site. In addition, the patient's response to each of the hearing tones (output locally) can be transmitted to the remote administration site where it can be considered and evaluated. Thus, the clinician can adjust the testing parameters based on the patient's response during the testing procedure. In so doing, the test administrator can, inter alia, (a) select or adjust the tone transmitted to the patient; (b) repeat one or more of the tones or frequencies; and/or (c) render a diagnostic evaluation.

Furthermore, in particular embodiments of the present invention, the test sequence and auditory hearing assessment tones may be controlled from the remote administration site and the tones generated locally so that they are output to the patient in a controlled calibrated manner. Embodiments of the present invention may also allow the test administrator (typically an audiologist) to adjust the test sequence or tone based on the patient's indicated response. Patient input or responses may also be accepted during the test and the associated data transmitted back to the administration site.

In certain embodiments, a portable, relatively inexpensive device which can operate independent of a personal computer may be provided. In other embodiments, a device which is configured to operate with a personal computer or other data processing system may be provided. Still other embodiments may allow the test to be generated by specialized software executing on a general-purpose data processing system. Thus, embodiments of the present invention may be configured to run locally utilizing a computer or other general-purpose data processing system in conjunction with a sound-generating device, or can be self-contained without requiring the use of a local general-purpose data processing system. In any event, embodiments of the present invention may also provide for management of the remote test by one or more computers at the test administration or expert site.

Embodiments of the present invention may also include patient-end devices which are configured to provide, in a calibrated or controlled manner, hearing assessment signals (speech and non-speech signals) in a plurality of different frequencies (such as 5-10 or more frequencies). In some embodiments, at least 8 different frequencies are evaluated during the test, with frequencies ranging between about 20-20,000 Hz, and more typically between about 125-12,000 Hz. The frequency of the tone may also be output to the user/patient with known intensity levels which may range from about 0 to about 120 dB (sound pressure level), depending on the test frequency. The hearing test, provided by the computer networked system, may be configured to generate tone presentations which meet ANSI standards, thereby providing, in some embodiments, a web-based testing protocol which meets recognized hearing diagnostic standards.

In some embodiments, a determination of whether environmental noise level meets a predetermined criteria at the patient or local site may also be made. For example, a local microphone or other sound detecting device may be used to detect the ambient noise level, either before or during the test, so that undue noise may be identified and the test restarted or delayed until a satisfactory environment is in place at the patient site. In some embodiments, this information can ascertain which type of headset or output device should be used by the patient at the local site.

Particular embodiments of the present invention may include specialized computer program signal processing and control algorithms and a local (patient-end) device configured to deliver the hearing assessment signals to the patient at the local computer via instructions provided over the computer network or web. The local device includes a transducer to transmit the test signals to the user. For example, the transducer can be a bone conduction oscillator, insert earphones or conventional supraaural earphones. Thus, the transducer can be held in a headset, earphones or other speaker output devices (such as hands-free devices including ITE (in-the-ear), BTE (behind-the-ear), and OTE (over-the-ear) devices) such that the hearing assessment signals travel directly into the ear canal(s) of the patient.

Alternatively, it is anticipated that the local transducer device can be desktop or handheld speakers operably associated with the local data processing system such that the hearing assessment signals travel through the air from a location away from the patient into the ear(s) of the patient (although such an output device may also indicate a need for a more controlled test environment to limit interference from undue environmental noise). This embodiment may also need to calibrate or control the output of the speakers (or apply a correction to the signals) to reliably calibrate the output signals across multiple types of general-purpose data processing systems. This embodiment may also need a more controlled testing environment, such as a sound-insulated booth.

In certain embodiments, in response to the hearing assessment signals associated with the web-based diagnostic hearing test, the patient interactively responds to the hearing assessment signals during the hearing test to identify when a hearing assessment signal becomes audible (such as by pressing a switch or button, clicking on the mouse, depressing a key on a keyboard, selecting an active region of a display, or speaking into a speech-recognition based microphone input system).

Alternatively, or in addition thereto, a biotelemetry mode may be used, wherein a local device measures middle ear pressure, compliance characteristics, changes and/or distortion product emission levels. These biotelemetry measures can be obtained with tympanometry as well as the measurement of otoacoustic emissions associated with cochlear hair cell responses in the ear (such as distortion product emission, transient and/or spontaneous). In operation, in some embodiments, the local device can be locally activated upon commands transmitted from a remote site such that the local device obtains the measurement without requiring patient interaction (the latter may then be used, for example, in young children and infants to diagnose abnormalities and/or hearing impairments), the diagnostic information can then be relayed through the computer network to the remote site during the test. In some embodiments, the information can be provided to the remote site and evaluated in a substantially "real time" manner.

In particular embodiments, the diagnostic test is simulcast (preferably as a two-way video conference) between an audiologist or therapist at the remote end and the patient at the local end. In other embodiments, a one-way video image (from the patient to the clinician at the test administration site) can be used. The audiovisual (or visual alone) communication can allow dynamic real-time communication to and from the patient and a physician or therapist located at the remote site during the diagnostic test. Such a simulcast or visual communication may occur within or outside the computer network.

In certain embodiments of the present invention, the hearing signals may be controlled so that each test signal is within about 1% of the indicated value and so that the harmonic distortion meets predetermined (typically ANSI) values to provide a reliable standardized full hearing range diagnostic evaluation.

In further embodiments of the present invention, hearing assessment signals are delivered at multiple frequencies across a wide frequency band and the signal intensity level is also controlled. Such control may be independent of any variable volume control action by the patient. Preferably, the signal intensity of the diagnostic hearing tests is controlled by the clinician or expert at the administration site and the command therefrom is relayed over a web-based system to a local device which includes a sound generator. In turn, the patient can respond to the test signal (by clicking or inputting to a keyboard, activating a switch, touching a screen or speaking into a microphone which may include voice recognition software) so that the remotely located clinician (at a data processing system remote from the user) is able to determine when the tones or signals become audible to the patient.

One embodiment of the present invention is a method for performing a hearing evaluation test over a computer network. The method includes the steps of: (a) administering a hearing evaluation test to a patient using a computer network, the hearing evaluation test comprising a plurality of hearing assessment signals at selected frequencies and hearing levels;

(b) transmitting commands from a test administration site to a local patient testing site during the administering step; (c) generating the hearing assessment signals at the local patient site in response to the transmitting step; and (d) interactively relaying information between the patient located at the local site and a clinician located at the test administration site during the administering step so that the clinician can evaluate the patient's response to the hearing assessment signals, the test administration site being remote from the local site.

The method can be performed such that the hearing evaluation test assessment signals are sufficient in number and variation of frequency and sound intensity to allow the clinician to perform a diagnostic hearing evaluation.

Similarly, another embodiment of the present invention is a method for delivering a diagnostic hearing test over a global computer network from a test administration site to a patient site, comprising the steps of: (a) generating, at a patient site, a plurality of hearing assessment signals at frequencies in the range of about 20-20,000 Hz; (b) transmitting, to the patient, a plurality of hearing assessment signals from the generating step, the plurality of hearing assessment signals being sufficient in number and variation of frequency and sound level intensity to provide enough information to the test administration control site to allow a diagnostic hearing evaluation to be performed by a clinician thereat according to predetermined standards; (c) controlling the output of the hearing assessment signals which are relayed to the patient during the transmitting step at a local site from a test administration site which is remote from the patient site, wherein said controlling step is carried out such that a clinician at the test administration site determines which hearing assessment signals of the generating step are relayed locally to the patient, (d) accepting patient input indicating when each of the plurality of hearing assessment signals from the transmitting step becomes audible thereto during the transmitting step; and (e) diagnosing the hearing ability of the patient at the test administration site.

Yet another embodiment of the present invention is a method of controlling a hearing test, which includes the steps of: (a) serving web pages from a web server associated with a hearing test device to a web client which indicate a status of the hearing test; (b) receiving requests from the web client which provide parameters for performing the hearing test; and (c) controlling operation of the test device based on the parameters of the received request from the web client so as to provide control of the hearing test. The hearing test can be a diagnostic hearing test and/or a biotelemetry measurement of the ear.

Another embodiment of the present invention is a hearing evaluation device. The device includes a web server, a diagnostic test device operably associated with the web server and configured so as to be controlled by the web server. The web server is further configured to serve web pages to a web client which indicate a status of a diagnostic hearing test, receive requests from the web client which provide parameters for performing the diagnostic hearing test, and control operation of the diagnostic test device based on the parameters of the received request from the web client.

An additional embodiment is directed to a hearing evaluation device for generating hearing assessment signals at a local patient site, comprising: (a) a processor configured to communicate over a computer network; (b) a tone generator operably associated with the processor, wherein, in operation, said tone generator is configured to generate tones at a plurality of selected frequencies in the frequency range of between about 20-20,000 Hz; (c) an output device operably associated with the tone generator, wherein, in operation, the output device adapted to deliver the tones of the hearing assessment signals to a patient undergoing a hearing evaluation; and (d) an input device operably associated with the processor. The input device is configured to indicate a patient's response to each of the tones of the hearing assessment signals, and the hearing evaluation device is configured to receive commands from a remote site through the processor computer network to select and adjust the tones generated by the tone generator.

Other embodiments of the present invention are directed to methods for performing a hearing evaluation test over a computer network, comprising the steps of (a) obtaining at least one of a tympanometric measurement of middle ear pressure and compliance or the measurement of evoked otoacoustic emissions of a patient using a computer network; (b) transmitting commands from a test administration site to a local patient testing site during (at least a portion of) the obtaining step; (c) generating the hearing assessment signals at the local patient site in response to the transmitting step; and (d) relaying data between the local site to a clinician located at the test administration site during at least a portion of the obtaining step so that the clinician can evaluate the patient's response to the hearing assessment signals, the test administration site being remote from the local site.

Still other embodiments are directed to methods of controlling an electrophysiological test involving one or more of evaluating otoacoustic emissions and tympanometry, the method comprising the steps of: (a) serving web pages from a web server associated with an otoacoustic auditory evaluation test device configured to measure otoacoustic emissions including at least one of middle ear compliance and cochlear hair cell responses, to a web client which indicates a status of the otoacoustic evaluation test; (b) receiving requests from the web client which provide parameters for performing the otoacoustic evaluation test; and (c) controlling at least a portion of the operation of the test based on the parameters of the received request from the web client.

As will be appreciated by those of skill in the art in light of the above discussion, the present, invention may be embodied as methods, systems and/or computer program products.

BRIEF DESCRIPTION OF THE DRAWINGS

FIGS. 14A-14C illustrate examples of data (stimulus and response parameters) of an electrophysiological auditory evaluation, which may be presented to the expert for measurement or analysis of distortion product or transient evoked otoacoustic emissions (TEOAE) according to embodiments of the present invention.

DETAILED DESCRIPTION OF EMBODIMENTS OF THE INVENTION

Figure 1:
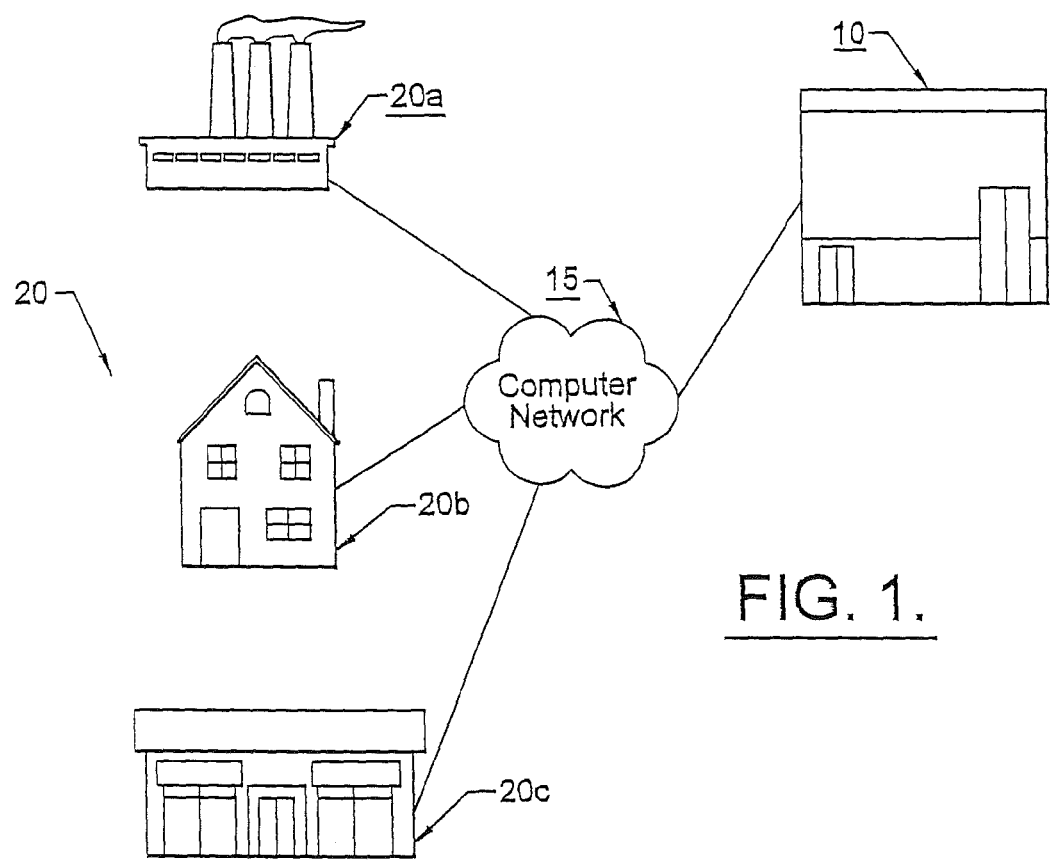
FIG. 1 is a block diagram of a network-computing environment which may provide communications between a test administration site and various patient test sites according to embodiments of the present invention.

The present invention will now be described more fully hereinafter with reference to the accompanying figures, in which preferred embodiments of the invention are shown. This invention may, however, be embodied in many different forms and should not be construed as limited to the embodiments set forth herein. Like numbers refer to like elements throughout. In the figures, layers, regions, or components may be exaggerated for clarity.

As will be appreciated by one of skill in the art, the present invention may be embodied as a method, data processing system, or computer program product. Accordingly, the present invention may take the form of an entirely hardware embodiment, an entirely software embodiment or an embodiment combining software and hardware aspects all generally referred to herein as a "circuit." Furthermore, the present invention may take the form of a computer program product on a computer-usable storage medium having computer-usable program code means embodied in the medium. Any suitable computer readable medium may be utilized including hard disks, CD-ROMs, optical storage devices, a transmission media such as those supporting the Internet or an intranet, or magnetic storage devices.

Computer program code for carrying out operations of the present invention may be written in an object oriented programming language such as Java®, Smalltalk or C++. However, the computer program code for carrying out operations of the present invention may also be written in conventional procedural programming languages, such as the "C" programming language. The program code may execute entirely on the user's computer, partly on the user's computer, as a stand-alone software package, partly on the user's computer and partly on a remote computer or entirely on the remote computer. In the latter scenario, the remote computer may be connected to the user's computer through a local area network (LAN) or a wide area network (WAN), or the connection may be made to an external computer (for example, through the Internet using an Internet Service Provider).

The present invention is described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions specified in the flowchart and/or block diagram block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart and/or block diagram block or blocks.

As noted above, the present invention provides systems, methods and associated devices for performing interactive diagnostic hearing tests which use a computer network to allow interaction between a test administration site and one or a plurality of remote ("local") patient sites. The term "patient" refers to the individual(s) being tested and can include the user, subject, or client at the local site. As shown in FIG. 1, the test administration site 10 can be a medical center or university or other desired location from which one or more clinicians or audiologists can administer the test. As is also shown, the test is relayed from the test administration site 10 to a desired patient or local site 20 through the use of a computer network 15. The local site 20 can, for example, be a factory or industrial office 20a, a medical related facility 20c, such as a hospital, general practice clinic, or pediatrician's office, and a primary residence or home 20b. The computer network 15 can be a local area network, a wide area network or a direct connection and may include an intranet (computers connected within a particular organization, company, coalition, or group), an extranet, a Virtual Private Network (VPN), the Internet, including the World Wide Web or other such mechanism for allowing a plurality of data processing systems to communicate.

In operation, the test is administered by a clinician or audiologist at the test administration site 10, remote from the patient site 20, in a manner which can allow interaction (typically one or more of a non-verbal, verbal, and/or visual communication interaction either one or two way) between the user and the clinician during at least a portion of the administration of the test. The diagnostic hearing tests can be performed such that they meet or comply with standardized guidelines such as the American National Standards Institute ("ANSI") requirements or other agency or regulatory standards, as desired for the particular testing authority in a particular jurisdiction.

In certain embodiments, multiple tests can be carried out concurrently by the test administration site communicating with multiple particular use/local patient sites utilizing, for example, different network addresses for the test administration site, the local patient sites or both. In some embodiments, the network address of the particular test site/device, as well as the date and time of the test, can be used to identify or correlate the test results to a patient, and allows the use of a patient specific identifier to be tracked therewith.

As described above, the system can be configured to allow the clinician at the test administration site 10 to control the test sequence and auditory hearing assessment tones from the remote administration site. Thus, the hearing test can be performed such that the hearing tones (frequency and decibel level) are generated and output locally at the patient site 20 in response to commands selecting the desired tone/level which are transmitted from the expert or test administration site to the local site via the computer network. In turn, the local system 20s, based on the received or relayed commands, generates the tones and controls the levels output to the user/patient locally so that they are output to the patient in a controlled calibrated manner. In certain embodiments, the system is also configured to accept the patient's input or response during the test and transmit the associated data back to the administration site where it can be considered and evaluated. The system can also allow the test administrator (typically an audiologist) to adjust the test sequence or tone based on the patient's indicated response during the testing protocol. Thus, the clinician can adjust the testing parameters or protocol based on the patient's response during the testing procedure. In so doing, the test administrator can, inter alid: (a) select or adjust the tone transmitted to the patient, (b) repeat one or more of the tones or frequencies, and/or (c) render a diagnostic evaluation.

In particular embodiments of the present invention, the test devices at the local sites 20a, 20b and 20c operate as servers and the data processing systems at the test administration site 10 operate as clients. In particular, the test devices may be web servers and the clients at the test administration site 10 may be web browsers. Accordingly, conventional client-server techniques may be modified as described below to provide remote control of the test devices by a client remote from the test devices. Such a web server/web browser approach may allow for utilization of existing computer network infrastructure, such as the Internet, the World Wide Web, intranets and extranets to provide for remote control of test devices without requiring a dedicated communication infrastructure. Furthermore, given the ubiquitous nature of the Internet, test devices may readily be moved from site to site. Additionally, additional security functionality may also be provided. For example; incorporation of a communication protocol stack at the client and the server supporting Secure Socket Layer (SSL) communications or Virtual Private Network (VPN) technology such as Internet Protocol Security Architecture (IPSec) may provide for secure communications between the patient sites 20a, 20b and 20c and the test administration site 10 to thereby assure a patient's privacy.

Figure 2A:
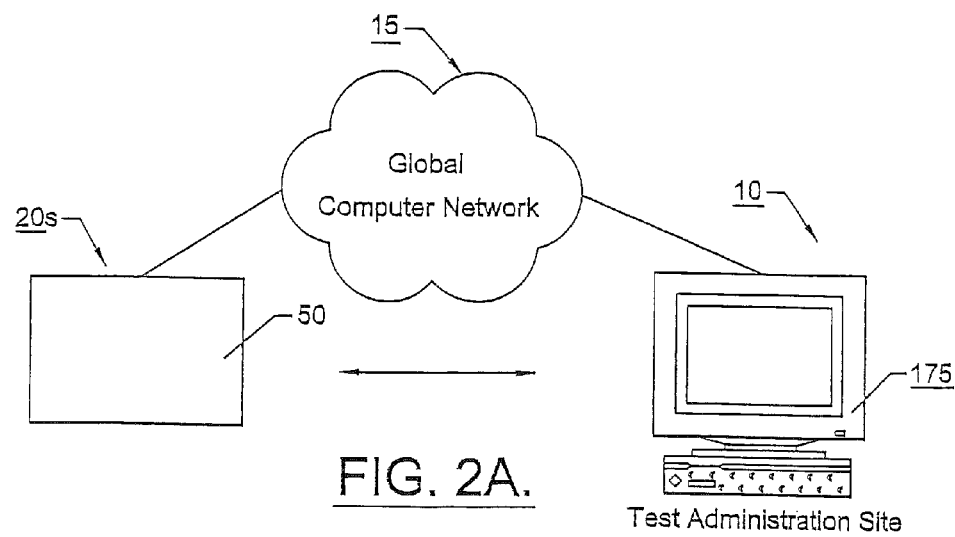
FIG. 2A is a block diagram of a network-computing environment having a test administration site and a local device used by the patient according to embodiments of the invention.
Figure 2B:
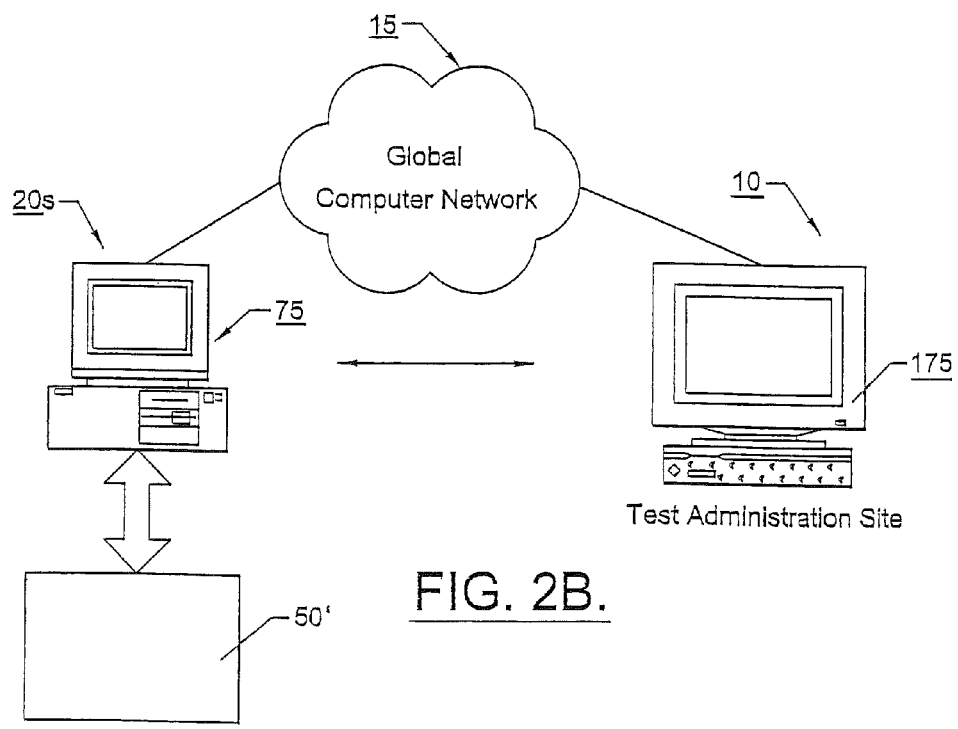
FIG. 2B is a block diagram of a network computer environment having a test administration site and a local device configured to communicate with a local general-purpose data processing system according to embodiments of the present invention.

In certain embodiments, as illustrated in FIG. 2A the local system 20s is configured as a portable relatively inexpensive self-contained device 50, which can operate independent of a personal computer and is configured to interface with a computer network 15. In other embodiments, as shown in FIG. 2B, the local system 20s can include a device 50' which is configured to operate with a personal computer 75 or other general purpose data processing system. Still other embodiments may allow the test to be generated by specialized software and a general-purpose data processing system such as a personal computer. Thus, the system can be configured to run locally off of a computer with a sound-generating device, or can be self-contained without requiring the use of a local computer. In any event, the system can be managed by one or more computers 175 at the test administration or expert site 10.

The system can include patient-end devices 50, 50' which are configured to provide, in a calibrated or controlled manner, hearing assessment signals (speech and non-speech signals) in an plurality of different frequencies (such as 5-10 or more frequencies). In some embodiments, at least 8 different frequencies are evaluated during the test, with frequencies ranging between about 20-20,000 Hz, and more typically between 125-12,000 Hz. The frequency of the tone will also be output to the user/patient with known intensity levels ranging from about 0 to about 120 dB (sound pressure level), depending on the test frequency. The hearing test, provided by the computer networked system, is able to generate tone presentations which meet ANSI standards, thereby providing, in some embodiments, a web-based testing protocol which meets recognized standardized hearing diagnostic standards.

Figure 3:
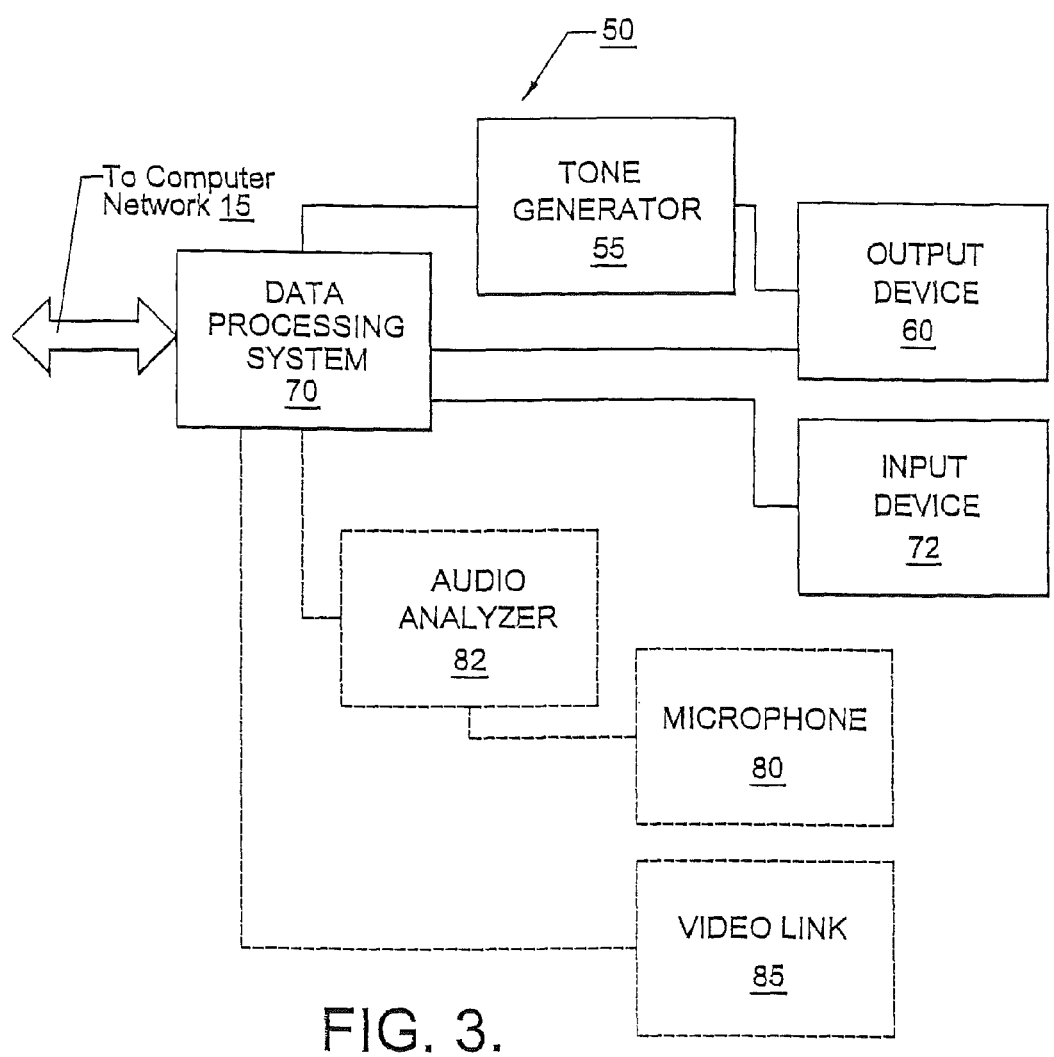
FIG. 3 is a block diagram of the local or patient end portion of a system according to one embodiment of the present invention.

Referring now to FIG. 3, one embodiment of a local device 50 is illustrated. As shown, the device 50 includes a tone generator 55, an output device 60, an input device 72, and a data processing system 70. The output device 60 can be a transducer such as a bone conduction oscillators or vibrators, insert earphones (i.e., over-the-ear ("OTB"), in-the-ear ("ITE"), behind-the-ear ("BTE")), or conventional supra-aural earphones. In some embodiments, it is anticipated that speakers may also be acceptable output devices.

The data processing system 70 is configured to provide the control and communication interface between the local device 50 and the remote test administration site 10. The data processing system 70 may be any data processing system capable of carrying out the operations described herein for controlling and providing communications with a computer network. Thus, the data processing system may be a general purpose data processing system, such as a personal computer, a specialized data, processing system such as a digital signal processor or embedded microprocessor, a network appliance, such as micro web servers or even pervasive computing devices such as personal digital assistants, smartphones or the like.

The data processing system 70 can receive commands from the clinician at the test administration site over the communications link to the computer network 15 to command the tone generator 55 and can also receive responses from the patient which it then can transmit over the communication link to the computer network 15 to the clinician. The communication link to the computer network 15 is illustrative of various suitable communications mechanisms that allow the local device 50 to communicate with the test administration site over a computer network. Such a communications link may be provided, for example, by a network interface of the data processing system. Typical network interfaces may include Ethernet, Token Ring or other such direct connections to a computer network provided, typically, by network interface card (NICs) or may be provided by, for example, a modem, including cable modems, Digital Subscriber Loop (DSL) modems, including ADSL. an sDSL modems, wireless modems or conventional telephone modems which provides communications to a computer network. The communications interface and a micro web server embodiment will be discussed further below.

The tone generator 55 is configured to generate the desired frequency tone at the desired level and transmit the tones to the output device 60. The tone presentation of the hearing signal generated by the tone generator 55 may be "continuously on" or manipulated to present a "pulse tone." One example of suitable testing protocols is shown in Table 1.

TABLE 1

Frequency and maximum hearing levels for device

| Frequency (Hz) | Hearing Levels (dB HL) | |
|---|---|---|
| | Air | Bone |
| 125 | 70 | |
| 250 | 90 | 45 |
| 500 | 120 | 60 |
| 1000 | 120 | 70 |
| 2000 | 120 | 70 |
| 3000 | 120 | 70 |
| 4000 | 120 | 60 |
| 6000 | 110 | 50 |
| 8000 | 100 | |
| 12000 | 90 | |

The tone presentation may be adjusted or determined depending on the configuration of the output device in use or the particular testing protocol desired (different output devices may be used at different local patient sites typically depending on (a) the patient and (b) the noise associated with the testing environment). In certain embodiments, the pulse length is presented to the patient such that it does not exceed about 225±35 ms. For air conducted signals, the tone is typically transmitted to the user for at least about 20 ms and such that it is equal to or less than about 50 ms. For bone-conducted signals, the rise or onset time shall be no less than 20 ms. When the tone is terminated, the "fall" time is less than about 20 ms. The duration of the tonal plateau can be presented to the patient such that it is equal to or above about 150 ms.

As shown above in Table 1, the testing protocol can include 10 different frequencies ranging from 125 Hz to 12000 Hz. Additional or lesser frequencies can be used, depending on the applicable test standard, although typically, the test frequencies will be between 20-20,000 Hz. The frequency accuracy for each test signal tone generated can be presented to the patient such that the signal is within about 1% of the indicated tone frequency.

In certain embodiments, the hearing assessment presentation signals can include frequency tones, narrow band noise, broadband noise, recorded noise and speech, as well as live speech. In certain embodiments, the device 50, 50' may also be configured such that the harmonic distortion of the tone frequencies, are able to meet the current ANSI standards, an example of a current standard ANSI-S3.6 1996 is listed in Table 2. Thus, in certain embodiments, the maximum level of the harmonics of the test tone relative to the level of the fundamental may be presented so as to not exceed the values given in Table 2 below.

TABLE 2

Maximum permissible harmonic distortion, expressed in percent *

| | Air Conduction | | | | Bone Conduction | | |
|---|---|---|---|---|---|---|---|
| Frequency (Hz) | 125 | 250 | 500-4000 | 6000-16000 | 250 | 500-750 | 1000-5000 |
| Hearing level | 75 | 90 | 110 | 90 | 20 | 50 | 60 |
| Second harmonic | 2 | 2 | 2 | 2 | 5 | 5 | 5 |
| Third harmonic | 2 | 2 | 2 | | 2 | 2 | 2 |
| Fourth & each higher harmonic | .3 | .3 | .3 | | 2 | 2 | 2 |
| All subharmonics | | .3 | .3 | .3 | | | |
| Total harmonic | 2.5 | 2.5 | 2.5 | 2.5 | 5.5 | 5.5 | 5.5 |

* ANSI-S3.6 1996

In operation, the desired hearing tone presentation is output to the output device 60 and to the patient. In response; the patient can indicate a response to the tone to the input device 72. The input device 72 can be a voice activated or speech recognition input microphone, or a physical input port such as a keypad, button, screen-contact software switch, or physical switch. In certain embodiments, the input device can be (or include) a video camera 85 which is video linked to the test administration site 10 so that the clinician can visually monitor the patient's response during the test. Further, two individually operable input devices can be employed, one for use when the patient acknowledges a tone to the right ear and one for when the patient acknowledges hearing from the left ear. It will be appreciated that, in some embodiments, the input device may be on the output transducer 60 headset itself as an alternative to the housing body of the device 50.

As is also shown in FIG. 3, the device 50 may, in some embodiments, include a microphone 80 to measure the ambient or environmental noise within the testing room or locale, at the patient site 20. This embodiment can allow the system to assure that the test complies with appropriate standards, such as ANSI S3.1-1999. This standard specifies the maximum permissible noise levels (MPANL) allowed in a room for audiometric threshold assessment. In certain embodiments, the microphone 80 can be configured to measure or detect sound pressure levels or noise in the range of between about 20 Hz to 20 kHz, and may, in some embodiments, detect sound pressure levels at octave intervals 125 to 8,000 Hz or up to 12,000 or greater Hz. The microphone 80 may operate prior to initiation of the testing procedure to determine what the noise or sound level is and if a particular type of output device 55 should be employed (such as whether supra-aural or insert earphones are appropriate to meet the applicable standard).

Sound Level Measurement of Ambient Noise

TABLE 3

Octave band ears covered maximum permissible ambient noise levels

| Octave Band Intervals (Hz) | Supra-aural Earphones | Insert Earphones |
|---|---|---|
| 125 | 39.0 | 67.0 |
| 250 | 25.0 | 53.0 |
| 500 | 21.0 | 50.0 |
| 1000 | 26.0 | 47.0 |
| 2000 | 34.0 | 49.0 |

TABLE 3-continued

Octave band ears covered maximum permissible ambient noise levels

| Octave Band Intervals (Hz) | Supra-aural Earphones | Insert Earphones |
|---|---|---|
| 4000 | 37.0 | 50.0 |
| 8000 | 37.0 | 56.0 |

Values are in dB re: 20 uPa to nearest 0.5 dB

In certain embodiments, the microphone 80 may be operable substantially continuously during the entire testing procedure to assess the noise during the test and to note either or both at the test administration site 10 or the local site 20 the detection of an undesirable ambient sound level or when or if a particular step or sequence should be repeated because of a detection of noise above a certain threshold level. The local system 20s may also include an audio analyzer 82 operably associated with the microphone 80 and the processor 70. The audio analyzer 82 can receive sound input from the microphone 80 and analyze whether the ambient noise level is suitable. The device 50 may include a visual indicator (90, FIG. 5) to note when the sound level is acceptable, unacceptable, or when it is approaching an impermissible level. A general threshold can be used for all types of devices, or can be monitored for the type of output device 60 used during a particular test. Examples of visual indicators (typically positioned at one or both of the local end 20 or test administration 10 sites) include multiple color light emitting diodes (LEDs) such as green and red LED's (and may include blue or yellow as well), or text or design/icon active matrix screen displays which visually affirm or identify the level and the like. The test administration site 10 can receive (upload) data regarding the ambient sound level before and/or during the test for evaluation during the procedure.

In other embodiments, a passive biotelemetry reading of the structure/operation of the ear (i.e., middle ear analysis, cochlea hair cell response, and the like) can be obtained. This measurement or reading can be administered in addition to (or separately from) the tone hearing test protocol. The biotelemetry sensor can be incorporated into the transducer output device 60 or can be an additional component. In operation, an operator at the test administration site can activate the local biotelemetry sensor in the ear of the subject and the associated measurement can be passively obtained (without requiring the subject to verbally or visually communicate). The measurement can be relayed to the test administration site 10 via the communication link to the computer network 15. As will be discussed below, the processor 70p associated with the patient site 20 can relay the information during the test by generating a webpage 70c and relaying that to a client at the test administration site.

The biotelemetry methods/systems can acquire multiple data sets and transmit them through the computer network to allow a remotely located clinician to generate a biotelemetry analysis of the auditory system of the patient. The multiple data sets can include data corresponding to otoacoustic emissions from either distortion product and/or transient approaches, middle-ear compliance (achieved from either single or multiple frequency stimulation and pressure) and/or acoustic reflex response. The local biotelemetry sensor may be activated/controlled by the remote site in a manner that allows for adjustment during the measurement and/or such that the data is relayed to the remote/test administration site in substantially "real-time" or at certain points in time during administration of the test. Embodiments of systems and methods related to web-based acquisition and analysis of transient and distortion product otoacoustic emissions and middle ear testing will be described further below.

Figure 4:
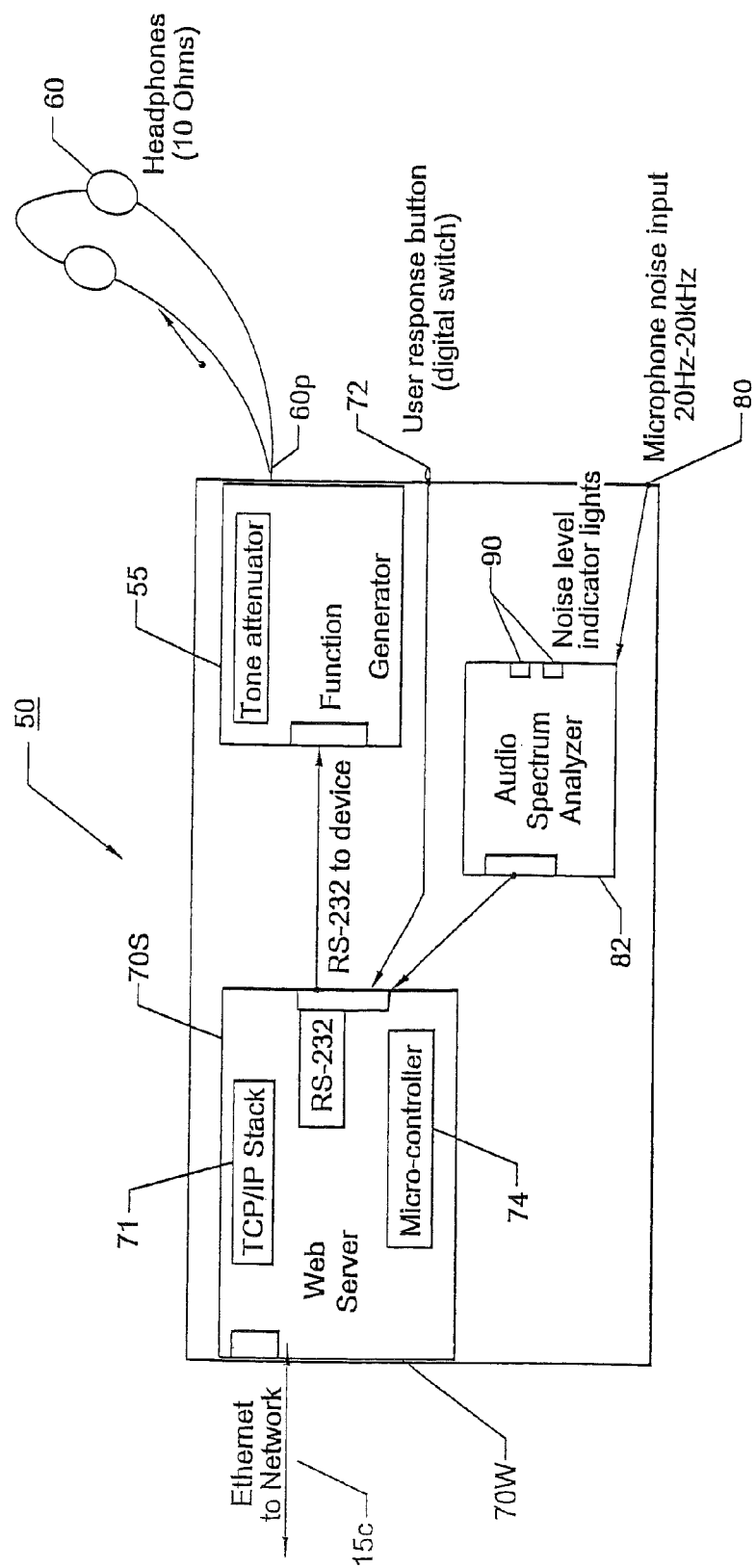
FIG. 4 is a block diagram of a portable device configured to locally generate and output the test signals in response to a remote command(s) from a test administration site according to embodiments of the present invention.

Turning now to FIG. 4, one embodiment of the local device 50 is shown. In this embodiment, the tone generator 55 includes a function generator (e.g. waveform generator) and a tone attenuator and headphones (10 Ohm) that are insertable into the output port 60p. As is also shown, the input device 72 is a digital switch. The microphone 80 is operably associated with an audio spectrum analyzer 82 which is connected to the microcontroller 74 through an RS-232 connection. The microphone 80 is preferably located away from the output device 60 so that it is able to pick up ambient noise. The device 50 can also be configured to filter out tones generated from the test itself in the ambient noise evaluation where the tones are transmitted through the air (not directly output to the ear). The audio spectrum analyzer 82 shown includes noise level indicator lights 90, which are visible to the patient during operation. The device 50 is configured to operate based on a web server 70w configuration and includes the microcontroller 74, an RS-232 bus and port 70s, a TCP/IP stack 71, and an Ethernet connection 15c to the computer network 15. Examples of suitable components such as the RX-11 Tonejack from Conex-Electro Systems (described at URL (www) conex-electro.com) which was modified to include an attenuator, and a Velleman K4300 Audio Spectrum Analyzer Kit available from Radio Shack as part no. 990-0171.

Figure 5:
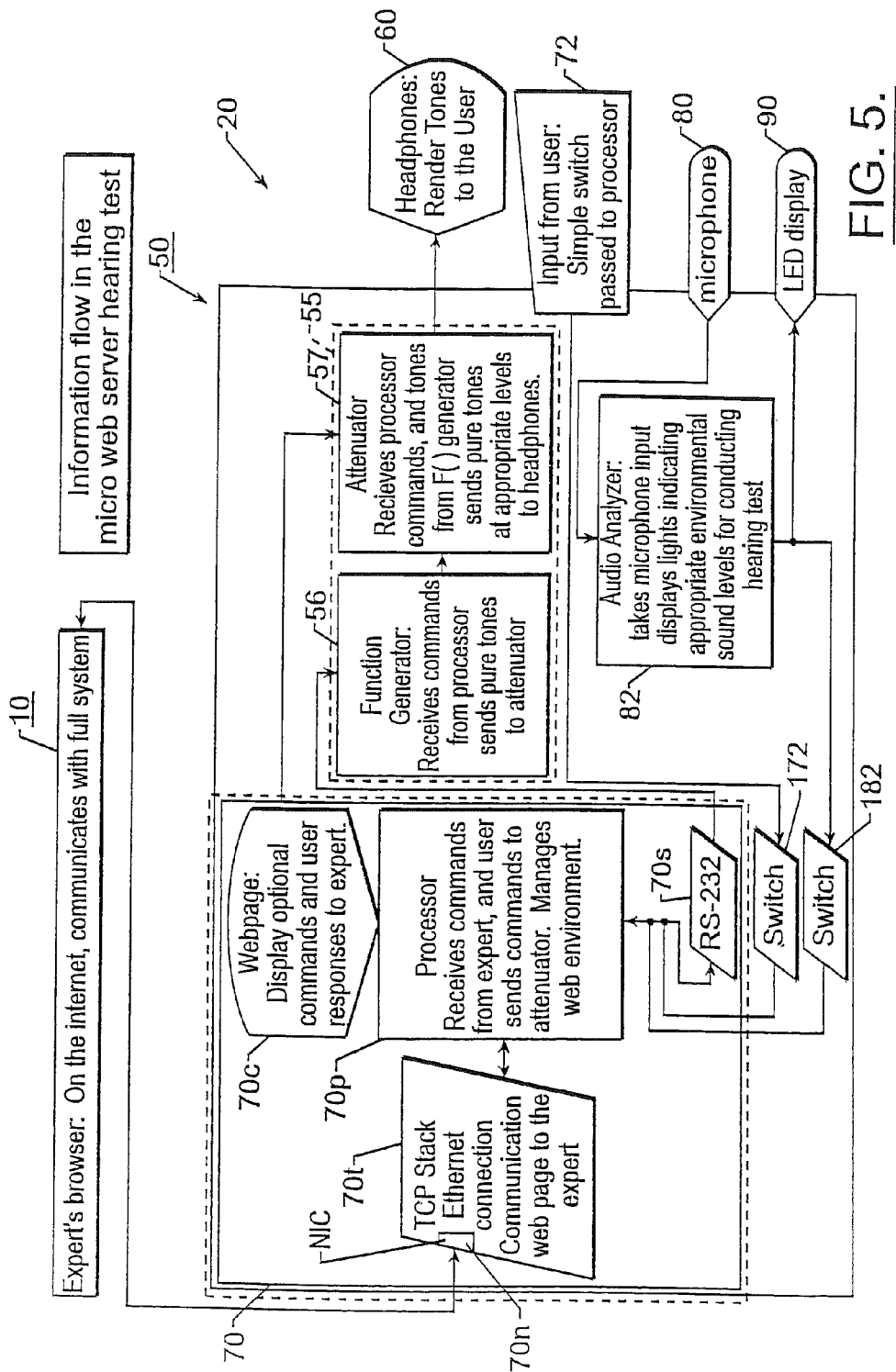
FIG. 5 is a block diagram of a portable device configured to operate independently of a local computer and to output test signals in response to a remote commands) from a test administration site according to embodiments of the present invention.

FIG. 5 illustrates a particular embodiment of the local device 50 according to embodiments of the invention where the data processing system 70 is a web server. In particular, the data processing system may be an Internet Appliance, such as a PICOSERVER by Lightner Engineering located in San Diego, Calif. (see also TJRL (www) picoweb.net) or other such web servers, including, but not limited to, those available from Axis Communications, or PICOWEB, RABBIT, and the like.

As shown, a processor 70p of the data processing system 70 receives commands from the clinician at the test administration site 10 and controls the function generator 56 and attenuator 57 to output the desired test sequence and tone to the headphones 60 to the client or patient. The data processing system 70 also includes a TCP stack 70t and Ethernet NIC 70n to provide the communication link 15c to the computer network 15 and to the test administration site 10.

The processor 70p provides information about the test to the test administration site 10 as web pages 70c which may be predefined and stored at the local device 50. Such web pages 70c may also be dynamically generated to incorporate test specific information. The web pages 70c may be Hypertext Markup Language (HTML) common gateway interface (CGI) web pages which allow for user input by a client, such as a web browser, of a user at the test administration site 10. The Web pages may also be or include Java scripts, Java applets or the like which may execute at the test administration site so as to control operations of an administration data processing system at the test administration site 10. As will be appreciated by those of skill in the art, other mechanisms for communicating between a web server and a client may also be utilized. For example, other markup languages, such as Wireless Markup Language (WML) or the like, for communicating between the local device 50 and the administration site 10 may be utilized.

When the test sequence and tone are output, the patient indicates when a test tone is audible, such as by depressing the input switch 72. The activation from the input switch is relayed back to the processor 70p via an internal directional switch 172 which generates and/or selects a web page 70c to be served to a client at the test administration site 10. In particular embodiments, the client at the test administration site is provide with a Java applet which causes the client to periodically request a web page from the local device 50. When the next web page is requested by the client, the processor 70*p* provides the generated and/or selected web page reflecting the activation of the input switch.

Similarly, the microphone 80 detects ambient sound and inputs the data associated therewith into the audio analyzer 82 which can determine the ambient noise level for the test and relay the information via a switch 182 to the processor 70*p*. The processor 70*p* can, in turn, relay the information to the test administrator during and/or before the test as described above by generating and/or selecting a web page 70*c* and serving that web page to a client at the test administration site 10.

Figure 6:
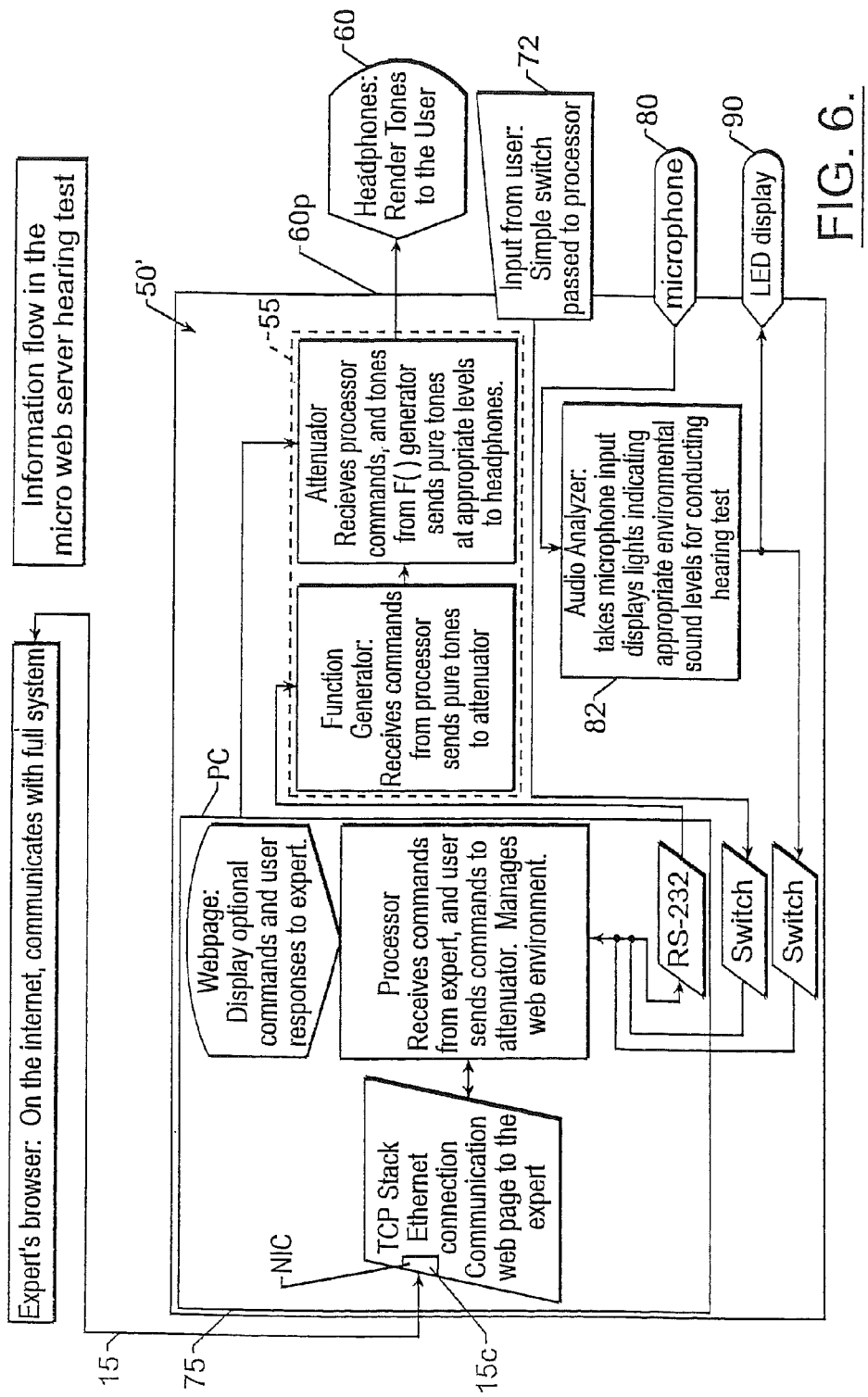
FIG. 6 is a block diagram of a portable device configured to communicate with a local computer and output test signals in response to a remote command(s) from a test administration site according to embodiments of the present invention.

Turning to FIG. 6, in other embodiments, the device 50' is configured to connect with a local computer such as a personal computer. The local computer 75 can be any suitable type whether a palm, laptop or desktop computer and the like. Alternatively, the local computer 75 may be pervasive computing device such as a smartphone or a PDA. Thus, in this embodiment, the device 50' includes the tone generator 55 and tone output port 60*p*. Optionally, in some embodiments, the device 50' may also include the microphone 80 and the audio analyzer 82. The device 50' may be provided as an internal for incorporation into the local computer 75 or as an external device. For example, the device 50' may be provided as a plug-in module, such as a "Springboard" for inclusion in a Visor PDA from Handspring. Alternatively, the device 50' may be a PCMCIA card which may be readily plugged into a laptop or other such general-purpose computer. Furthermore, the device 50' may be a separate unit which connects to, for example, the serial port of a general-purpose computer.

As shown in FIG. 5, the processor 70*p*, web pages 70*c*, TCP stack 70*t* and Enterhnet NIC 70*n* can be provided by the local computer 75. In this embodiment, the display screen and/or keyboard of the local computer 75 may be used as the input device 72 (or may be used along with an input device in the device 50'). Similarly, the video link described above may be provided by the local computer 75. The operational software needed to supplement the local operating system may be provided as a packaged product which is downloadable onto the local computer or may be provided at a URL location to be electronically downloadable therefrom.

Figure 7:
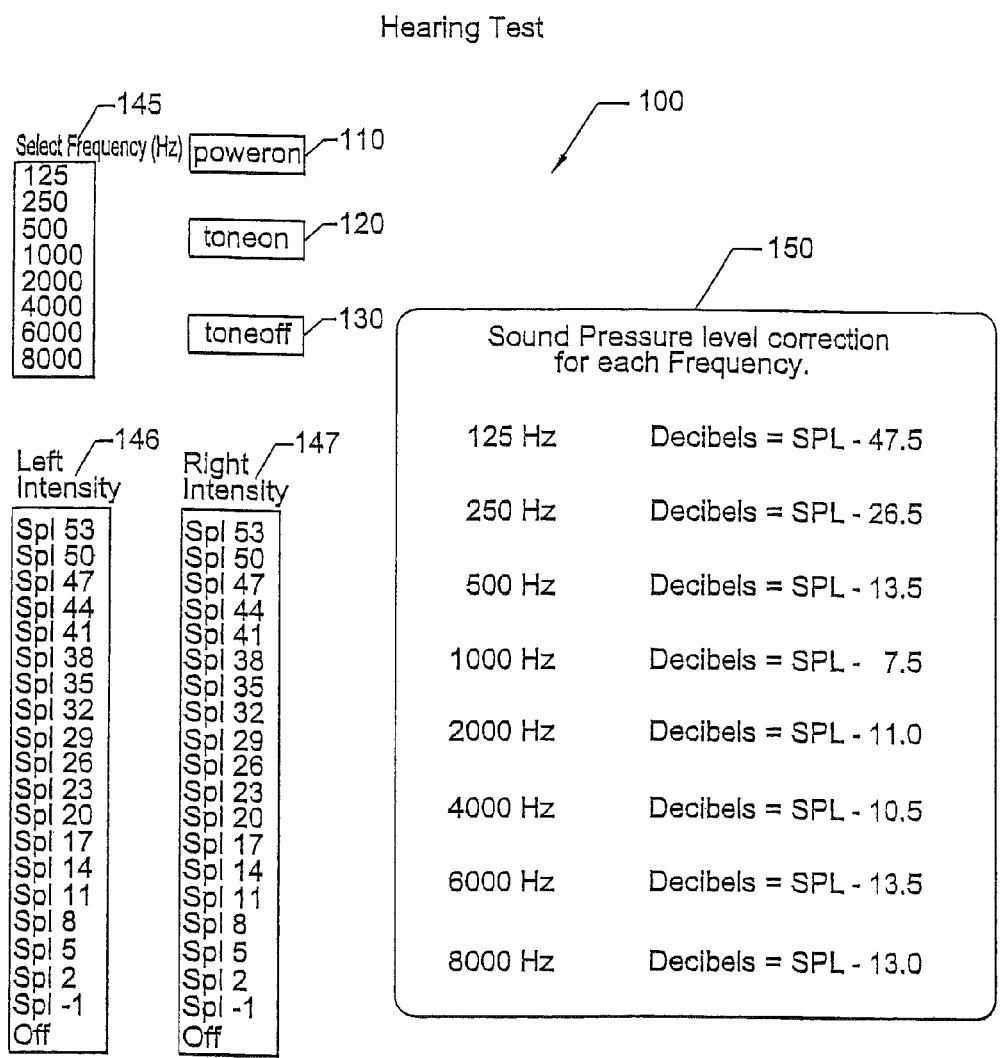
FIG. 7 is an exemplary screen printout of a web page at the test administration site which illustrates some of the selections the test administration site can make during the test according to one embodiment of the present invention.

FIG. 7 illustrates an example of a web page 100 which may be served to the test administration site 10 by the local device 50, 50' to allow control of the local device 50, 50'. As shown, this web page 100 may be provided from the server of the local device 50, 50' to a client, such as a web browser, at the test administration site 10 and includes test control parameters which can be activated and/or adjusted by the clinician during the test. The test parameters shown include a power on control 110, a tone on 120, tone off 130, selectable frequency, and independently selectable left and right intensity controls 146, 147. The power on control 110 can activate the tone generator 55 or function generator 56 at the local site 20 (deselecting this control then powers off or deactivates the tone generator 55). The tone on and tone off controls 120, 130 are typically operably associated with an attenuator and/or output switch and allows the clinician to control the length (or to initiate at desired intervals and terminate the sound when the response is indicated) of the tone signal output to the patient at the local site. The select frequency control 145 allows the clinician to adjust the test frequency and order of the testing protocol. The left and right intensity controls 146, 147 allow the clinician to adjust the intensity in the desired ear for each frequency selected. The data box 150 identifies the sound pressure level correction for each frequency. The exemplary screen display shown is for discussion purposes and, it is noted that, the screen layout, test parameters, and activation and/or control features may vary.

The illustrated controls may be selected by a user at the test administration site 10 by, for example, clicking on, touching, or pointing to, the particular control in displayed by the web browser. Such a selection may cause an indication of the selection to be transmitted to the web server of the local device 50, 50'. For example, a CGI response would be provided to the web server indicating selection of the power on 110 pushbutton. The CGI response would be parsed by the web server of the local device 50, 50' and the results used to control the state of the local device 50, 50'.

Figure 8:
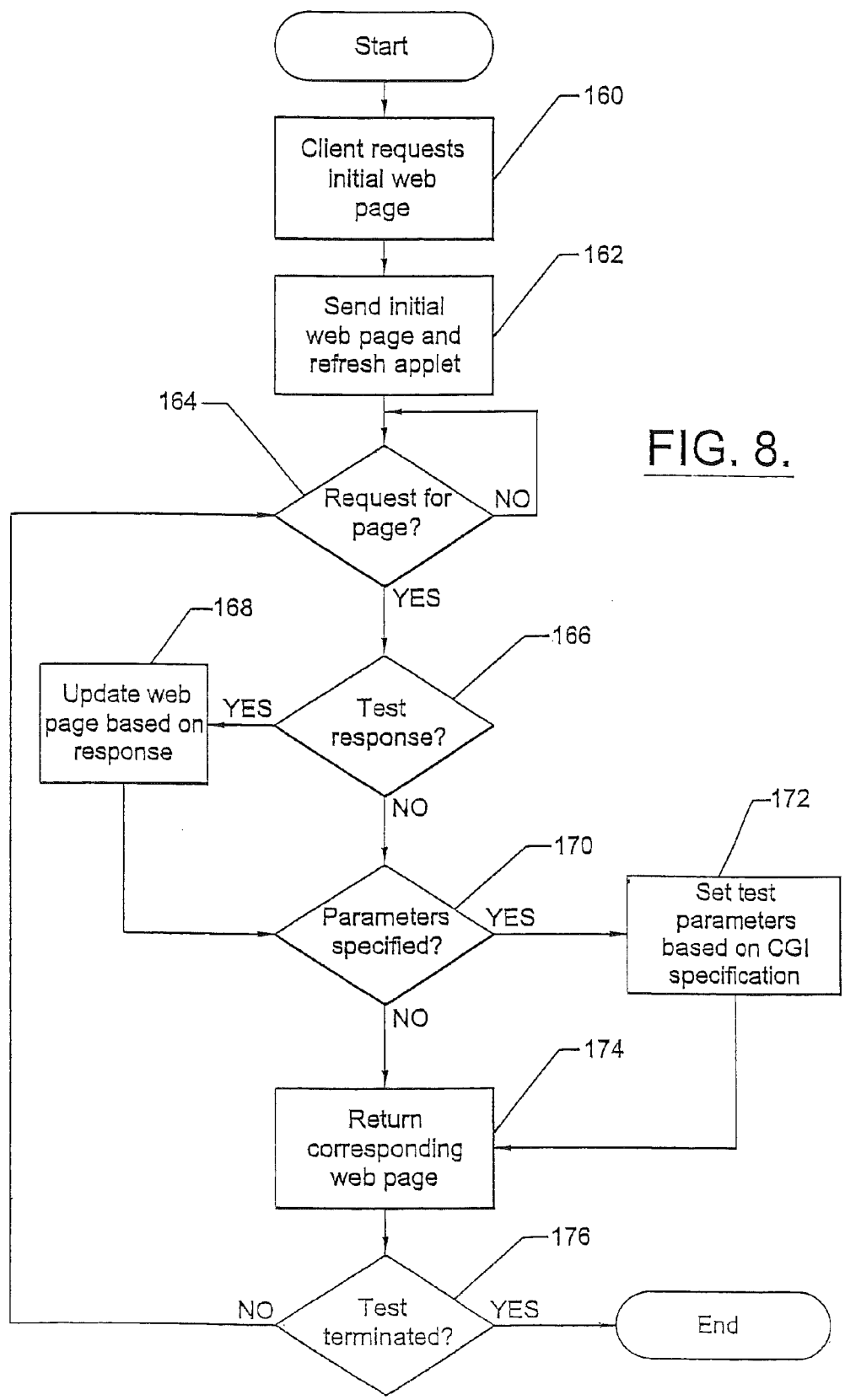
FIG. 8 is a flowchart of operations for performing a hearing evaluation according to embodiments of the present invention.

Operations of a web server and a web client according to embodiments of the present invention will now be described with reference to FIG. 8. As seen in FIG. 8, the client, e.g., the web browser as the test administration site 10, requests an initial web page from the web server of the local device 50, 50' (block 160). Such a request may take the form of an Hypertext Transfer Protocol (HTTP) request to the IP address of the web server of the local device 50, 50'. The IP address may be pre-assigned to the local device 50, 50' or may be dynamically assigned when the local device 50, 50' attaches to the network 15. Thus, the web browser may know in advance the IP address of the local device or may be notified of the IP address by a user at the remote site as part of a setup procedure.

When the local device 50, 50' receives the request for the initial web page, it sends the initial web page and a Java applet which causes the web browser to periodically reload its current web page (block 162). Alternatively, "push" technology could be employed by the server to push data to the web browser when status is to be updated. The rate at which the web page is reloaded may be based on the type of test being performed or the web page being displayed. Similarly, the rate may also be based on the type of network connection utilized such that for slower connection types the refresh rate could be reduced. While the embodiment illustrated in FIG. 8 illustrates providing the Java applet once with the initial web page, the Java applet could be provided with each web page and refresh rate could be based on the particular web page provided. For example, a setup web page could be refreshed less often then a test status web page (or not at all).

In any event, after the initial web page is provided to the web browser, the web server of the local devices 50, 50' waits for a subsequent request for a web page (block 164). When a request is received, it may be determined if the request is for a response to a test, such as activation of a switch or ambient noise level information, which is to be included in the responsive web page (block 166). If so, then the web page may be revised to indicate the information (block 168). In any event, it may also be determined if the request specifies parameters for the test (block 170) by, for example, providing a CGI request which reflects user input to the web browser. If so, the test parameters are set based on the CGI specifications (block 172) and the web page corresponding to the URL of the request is returned to the web browser (block 174). If the test is terminated (block 176), then operations may terminate. Otherwise, the web server waits for the next request from the web browser (block 164).

Figure 9:
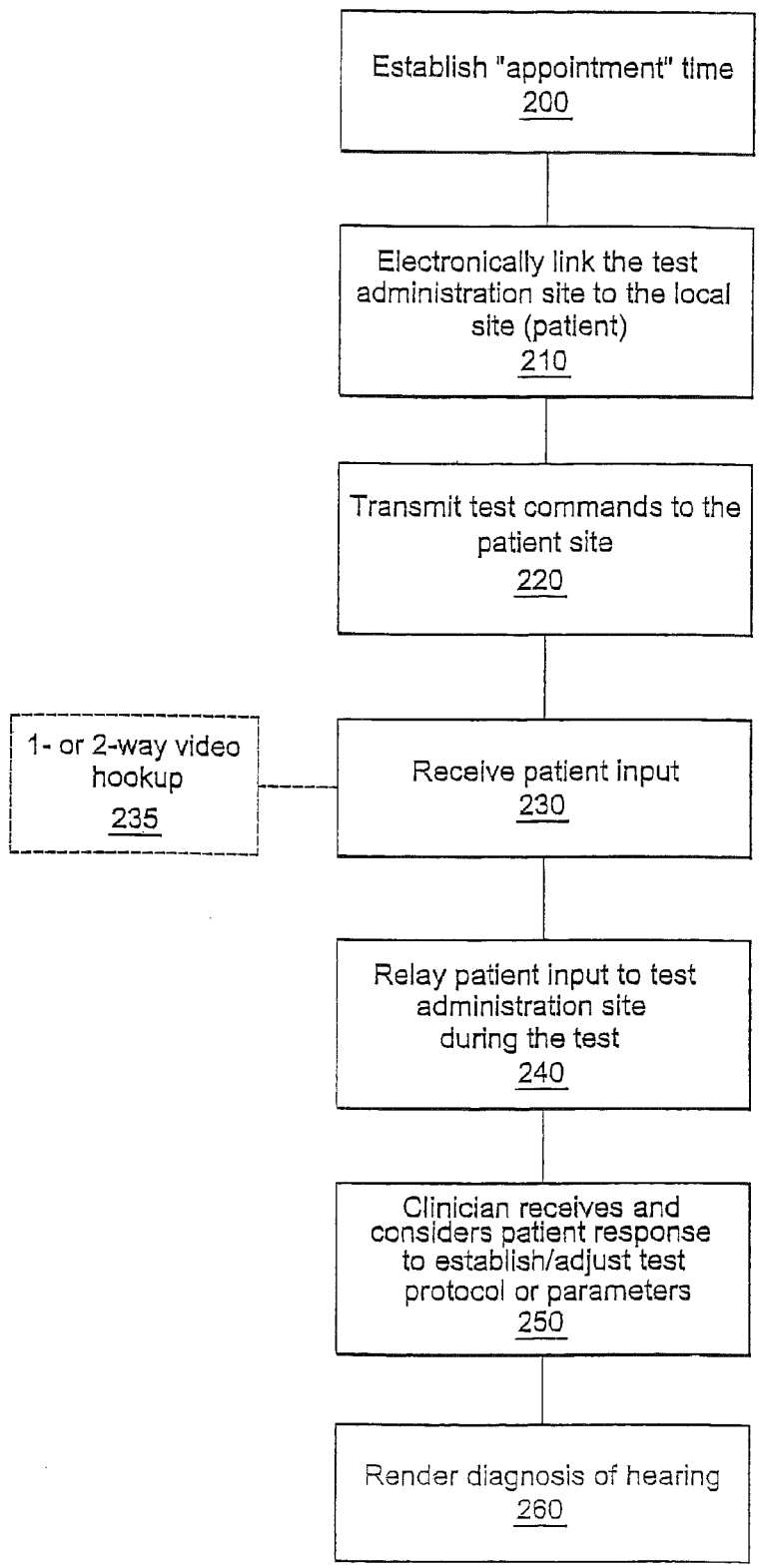
FIG. 9 is flowchart of operations for a hearing evaluation according to embodiments of the present invention.

FIG. 9 illustrates one embodiment of a method for administering a hearing test. As shown, an "appointment" time is established for the hearing test to be administered (to allow the interchange between the clinician and the patient) (block 200). The electronic communication link is established between the test administration site and the local patient site (block 210). The test commands are transmitted by the clinician to the local site during the testing protocol to generate the desired tone presentation to the patient (block 220). The patient's response to the test signal(s) is received during the testing protocol (block 230). The response can be a measurement taken from a probe in the ear as well as input to indicate when a tone is heard (which input can be visual, verbal or spoken, or contact such as keypad or switch) or a biotelemetry reading can be obtained automatically. Optionally, a one-way or two-way video link (or audio-video line) may be provided between the patient and clinician during the testing protocol (block 235). The patient response input can be relayed back to the clinician at the test administration site (block 240). The clinician receives and considers the patient response to establish/adjust the tet protocol or testing parameters (block 250). A hearing diagnosis can be rendered based on the information provided by the test (block 260).

Figure 10:
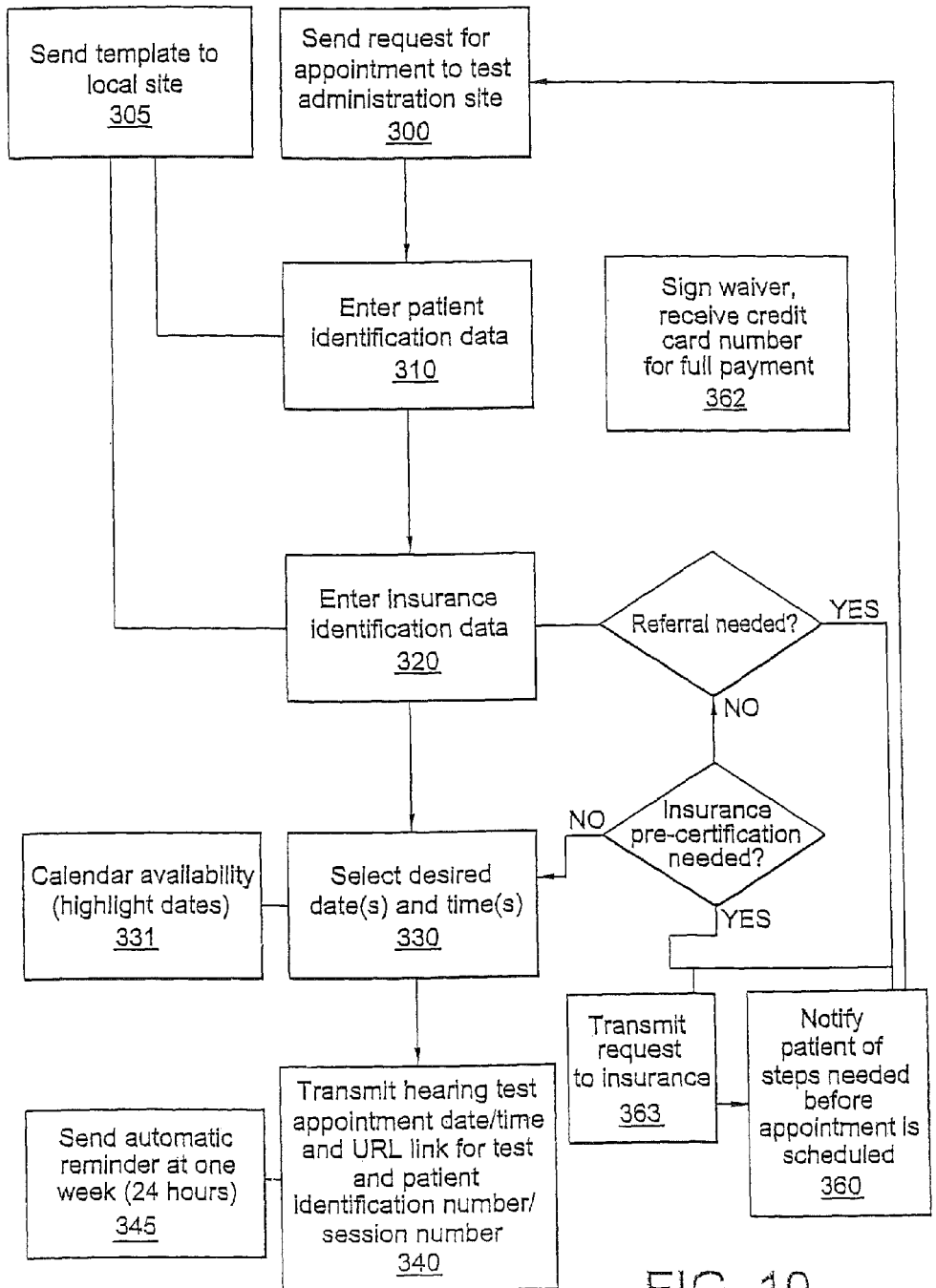
FIG. 10 is a flowchart of operations of a hearing evaluation scheduling method according to embodiments of the present invention.

In certain embodiments, as shown in FIG. 10, an appointment can be established by sending a request for an appointment to the test administration site (block 300). This can be telephonically established or can be established via the use of electronic mail (email) or other such communication including a chat session or the like. In some embodiments, a block of time may be pre-established for certain local sites such as hospitals, pediatrician's offices, and the like. Next, patient identification data can be entered into an electronic record (such as name, social security number, date of birth, referring doctor (as needed), and the like) (block 310). Insurance information can also be provided as needed (block 320) (such as policy, type, insurance pre-certification approval number, and the like). A template may be sent from the test administration site (block 305) to present data fields for the local site to complete to help build a complete record. Based on this information, the test administration site can verify whether a referral is needed to get insurance approval for the test based on a list of insurance policies and companies in a database or by contacting same. If a referral is indicated as needed, and no referral information has been entered in electronic record, the local site can be contacted to notify the patient (block 360). Similarly, if pre-certification or approval is needed from the insurance company which has not been obtained, the local site can be notified (block 360) and the test administration site may transmit the request to the insurance company (block 363). Alternatively, a "click" agreement can be entered whereby the local site/user provides a credit card number and agrees to assume full payment and bypasses the referral/insurance referral steps (block 362). In such embodiments, the local devices 50, 50' could operate as both a server and a client such that information could be provided from the test administration site to a browser or other client at the local device 50, 50'. The system can be configured such that any private information input as described above can be entered in secure/privacy procedures known to those of skill in the art, such as using a VPN or SSL as described above.

If all is in order, the local site can select the desired date and time (block 330). This can be done in several ways such as by selecting from a list of available time slots and dates provided from the test administration site. The available slots may be provided with the use of a calendar format (highlighting dates on which appointments are available during a month period). The local site can select by highlighting or clicking on the desired date and test time. The patient can be assigned a unique identifier/confirmation number. The test administration site can then electronically commence the communication link at the appointment time at the electronic address provided (block 340). This may be provided either by the email address or by the IP address or other electronic address identifier associated with the device 50, 50' which will be used for the test. Automatic reminders of the test date can be sent at desired intervals such as at 1 week/24 hours before the appointment time (block 345). This reminder can be by telephone or electronic mail.

Figure 11:
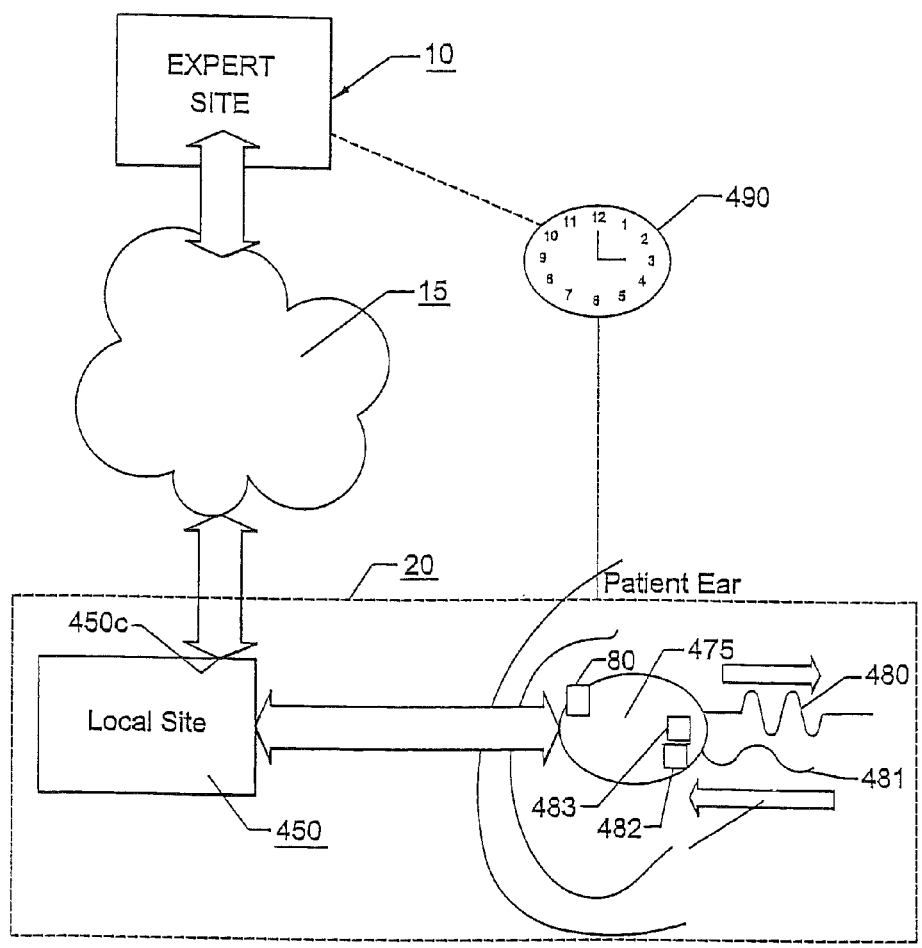
FIG. 11 is a schematic of a biotelemetry measurement system used to evaluate otoacoustic emissions and/or middle ear pressure and compliance characteristics according to embodiments of the present invention.

Turning now to FIG. 11, certain embodiments of the invention are directed to electrophysiological tests of audiological procedures for measuring otoacoustic emissions and/or using tympanometry and includes systems, methods, and devices which are configured to stimulate and obtain for evaluation, signals associated with the otoacoustic emissions and/or responses oracoustics reflexes of a subject via a computer network system. As before, the computer network can be a local, regional or global system such as the worldwide web (i.e., the Internet). As for the diagnostic hearing evaluation systems, in these embodiments, the system includes a patient end or "local" device 450 at a local site 20 and an expert end or "remote" device 10 which are operatively connected via the computer network 15. The local device 450 can be configured to interactively respond to commands sent from an expert at the remote site (such as a clinician or audiologist) during a portion, or all, of the testing procedure.

In operation, the local or patient end device 450 can stimulate one or more of the subject's ears (independently) via test signals and then detect one or more responses to provide multiple data sets associated with multiple parameters used to evaluate the subject's auditory response. The evaluated auditory responses can include one or more of (1) otoacoustic emissions from either (or both) distortion product or transient approaches, (2) middle-ear pressure and compliance characteristics (typically based on either a single frequency or multi-frequency stimulation and pressure), and (3) acoustic reflex response. Of course, the local device can be configured to provide both the hearing evaluations discussed above and the electrophysiological auditory response evaluation (each test type can be carried out with an integrated headset or a different headset, preferably employing a disposable single use probe assembly or ear insert device).

In certain embodiments, as shown in FIG. 11, the patient end device 20 includes an in-the-ear probe assembly 475 which is configured to transmit a stimulus signal or signals 480 into an ear of the subject and then sense (passively obtain) the desired emission or response signals 481. The detected or sensed response signals 481 are then relayed to the local device 450, where signal processing can occur, and then to the expert site 10 via the network 15 for evaluation. In operation, the test or stimulation signal 480 is output locally via the probe assembly 475 to the patient based on the desired test signals and/or parameters (and/or sequence) selected by the clinician at the remote site. In addition or alternatively, the parameters, sequence, or timing of the test may be altered or adjusted by the clinician at the remote site during the test. The clinician can, in certain embodiments, receive response data associated with the test stimulation protocol at certain intervals during the testing procedure or semi continuously or continuously during the test. The clinician can, as desired or needed, select, adjust, repeat, or test the other ear or otherwise manipulate the testing protocol during the evaluation depending on the patient's response or the detected ambient noise in the testing environment.

The local device 450 can include an environmental noise evaluation microphone 80 (as discussed for the device 50, 50') which can detect ambient noise before, or during, the test so that the remote site can determine the validity or reliability of the data. In some embodiments, the ambient noise data can allow the potentially corrupt data to be replaced by a supplemental test before the conclusion of the testing procedure, where needed. The microphone 80 may be positioned on the local device 450 (not shown). Alternatively, the microphone 80 may be positioned on the probe assembly 475 itself (such as on the portion of the probe assembly facing away from the inner ear). As an additional alternative, the microphone 80 may be positioned on a supplemental housing spaced apart from the probe assembly or mounted separately to the subject or otherwise disposed proximate the subject during the testing procedure (not shown). This may be helpful for infant testing where sneezing, coughing, and the like can be detected during the testing protocol.

As schematically shown by the clock 190 in FIG. 11, the system can be configured such that the remote expert site 10 is able to receive data and/or transmit requests to the local device 450 during the test in substantially real time or to Control the test (or a portion thereof, such as the initiation of the testing sequence, the change from one ear to another, or the upload of data). As used herein, the term "substantially real time" means receiving and/or transmitting data between sites during the test or temporally proximate in time thereto accounting for system delays in remote transmission between sites which may be seconds or minutes in length or longer as a result of routing, traffic, transmission route, and/or system communication link employed which can impede the transfer such that slight delays may occur.

The local device 450, as for devices 50, 50', can be configured as a stand alone device (as shown), preferably with signal and data processing capability, and remote communication link 450c (whether via one or more of wireless, tower or satellite transmission, cable, telephone, fiber optic, or other communication link) so as to be able to transfer or upload data to (and preferably from as well) the remote location. In certain embodiments, the local device 450 is portable and may be implemented as a pervasive computing device that is configured to generate the desired test signals and to receive the response signals and relay the information to the remote site via the communication link 450c. Alternatively, the local device 450 can be configured to be operably engageable with a local computer or pervasive communications device (whether stationary or portable such as a laptop, handheld, or other miniaturized device) during the test, which, in turn, may provide the modem or communication link to the network 15 and to the remote site. The device 450 may be configured to engage with a local computer or portable communications device or pervasive computing device via hardwired electrical connections, or wireless signal transmission including infrared data transmission means.

In certain embodiments, as before, the processing or control system associated with the local device 450 can be configured to relay the test data by use of a web server and web client. The web server and web client configuration may be such that a webpage is generated at the local site and relayed to the expert or test administration site. The webpage can be updated a plurality of times during the test to relay different data sets to the clinician during the test. In any event, the remote site computer can be configured to access the status of the local device, and to initiate the testing procedure or to upload data depending on the status determination. Thus, the local device can be configured to allow a local operator to power up and depress a "ready button" when the probe assembly is in position. Alternatively, the remote site can be used to power up the local device and to transmit status signal requests until the device is deemed to be in suitable position in the subject. As noted above, a camera may also be used to allow the remote site to visually note when the local device and patient are ready for the testing procedure.

Referring to FIG. 11, in operation, in certain embodiments, the local device 450 is configured to generate stimulation signals corresponding to the testing protocol associated with the desired test (such as middle ear compliance or distortion product type evaluations). The stimulation signals 480 are transmitted from an output source located in the ear probe assembly 475, such as one or more speakers 482 having suitable operating characteristics in the desired frequency range (such as model ER-2 speakers from Etymotic Research Corporation, believed to have a relatively flat response from about 200 Hz-10 kHz). The probe assembly 475 can also include one or more sensors 483 such as transducers and/or one or more miniaturized low noise microphones oriented and configured to sense signals evoked in the ear of the subject. The sensor 483 detects the evoked response signal and relays the signal (typically as a digital signal converted by an A/D converter, as well known to those of skill in the art) to the local device 450. The local device 450 can directly relay the detected signals in the form in which they are received. Alternatively, the local device 450 (or associated computer or signal processor) can process the received signals into a desired format before transmitting to the remote site. For example, the data processor or the digital signal processor in the local device 450 can generate a time dependent measurement profile of the response of a particular segment or portion of the test (i.e., a selected test segment) and then relay the profile(s) at selected times during the test, such as after a delay of 5 ms-30 seconds after each test stimulation sequence or segment or just prior to the initiation of the next testing sequence. The data transfer can be structured in any desirable format, such as to transfer data sets for each test segment and, where desired, transfer the relevant ambient noise data for the same time period. The data transfer can be performed in serially successive data uploads to update the webpage a plurality of times during the testing procedure.

Figure 12:
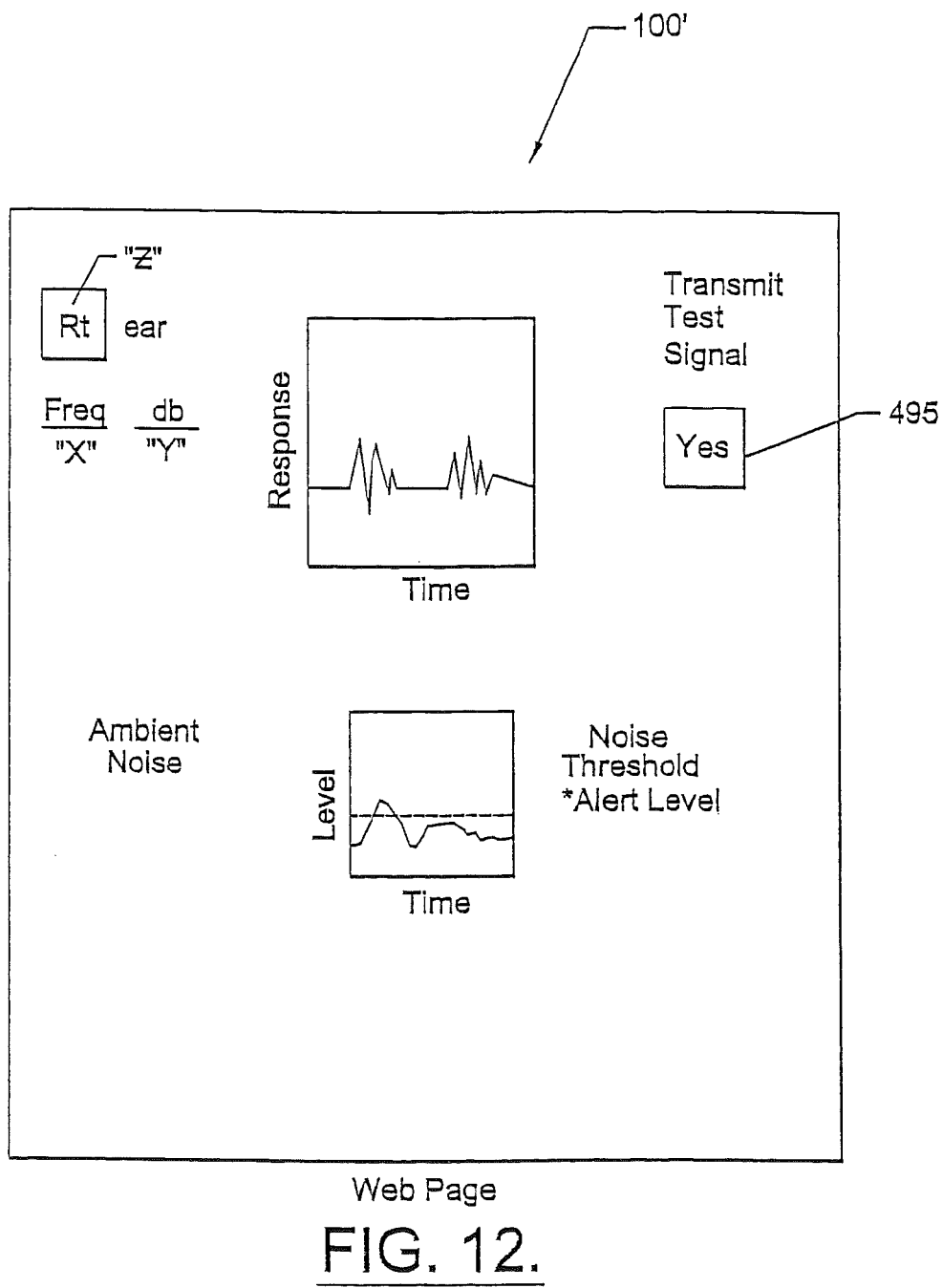
FIG. 12 is a simulated representation of a web page displaying time-dependent measurement data and test parameter selections according to embodiments of the present invention.

In any event, as shown in exemplary method steps in FIG. 8 and as a exemplary webpage in FIG. 12, the webpage 100' can be updated one or more times during the testing protocol or testing segment to show the detected time-dependent response (and may also show or indicate that the noise threshold is below or above a selected desirable threshold level). The webpage 100' may also allow the clinician to select the testing stimulation activation via a test activation button 495. The activation button can be used to activate the local device to relay the test signal(s) to the subject for a particular ear (shown as parameter "Z"), to allow the clinician to adjust or select a particular frequency (shown as parameter "X") or decibel or pressure level (shown as parameter "Y"), or merely to initiate or restart a standardized protocol, testing sequence or segment (a "segment" referring to a subset of the overall testing procedure).

For embodiments directed to the measurement of middle ear pressure and compliance characteristics through acoustic imittance, the present invention can allow the diagnostician (at the remote site) to passively analyze the characteristics of the middle ear. The system may be configured to present both a probe tone (typically at about, 226 Hz) and a change in air pressure to the ear canal undergoing analysis. The microphone of the device measures the amount of acoustic energy transmitted through the tympanic membrane. This reading is transmitted from the probe assembly 475 at the local site 20 via a web server for analysis at the remote computer site 10.

Figure 13:
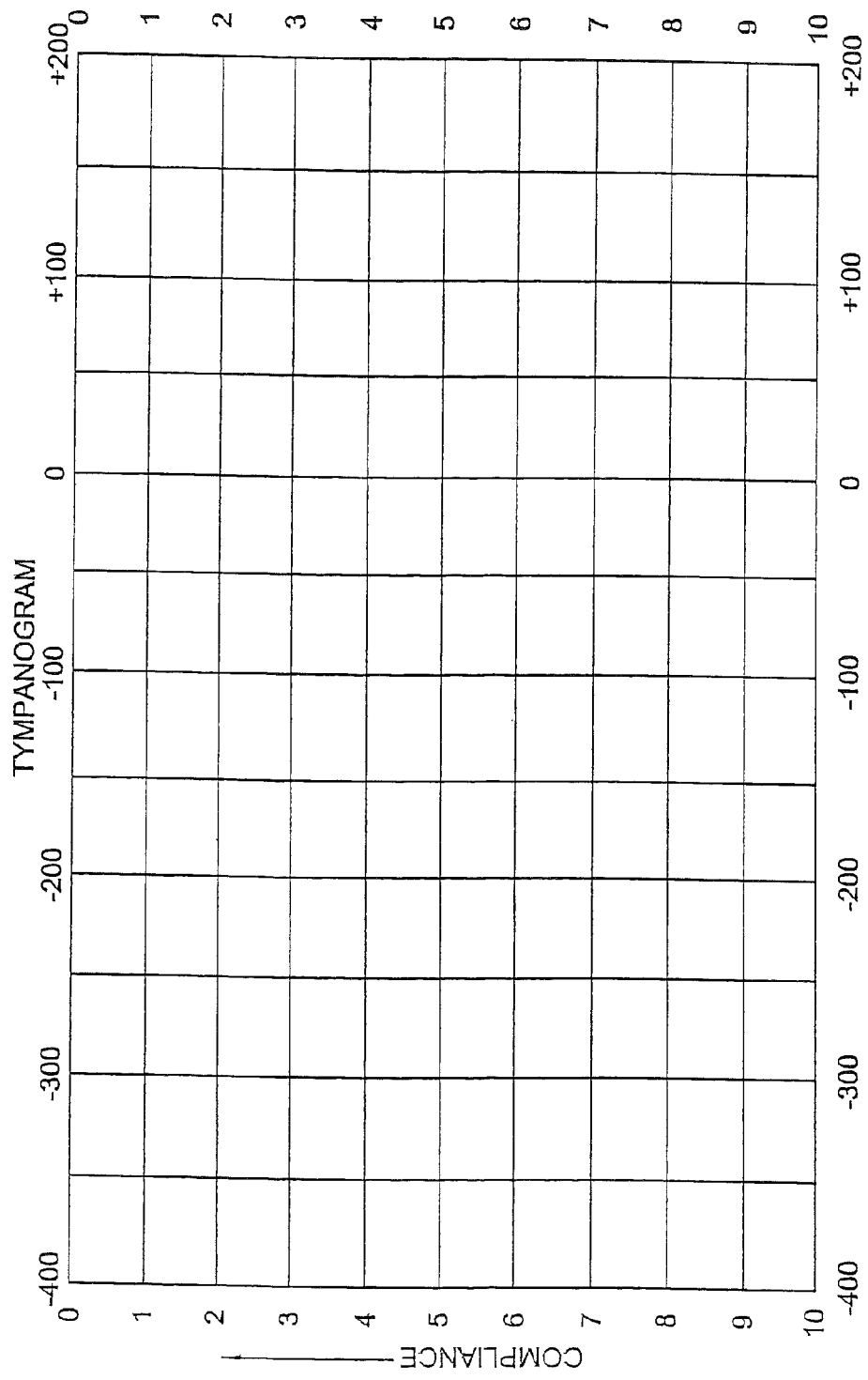
FIG. 13 is a graph of a sample tympanogram for compliance versus pressure which may be presented on a web page or expert computer according to embodiments of the present invention.

FIG. 13 illustrates a "tympanogram" or graph format of a tympanometric measurement test that may be electronically generated (or data corresponding thereto rendered) as a part of a web page or on the expert end computer during tympanometry evaluation of the patient. The vertical axis (from 10-0) corresponds to the measurement of compliance while the horizontal or "X" axis corresponds to the measurement of pressure (shown as values of between about −400-+200 daPa).

FIGS. 14A-C illustrates an exemplary web page format (that may be generated at the expert end of the system) with three different segments associated with measurement of evoked otoacoustic emissions. The upper graph in FIG. 14A illustrates a temporal waveform of the stimulus while the lower graph in FIG. 14A illustrates a spectral waveform of the stimuli (in frequency response, where a substantially flat waveform is desired). The data at the bottom of FIG. 14A corresponds to the peak stimulus intensity level (in dB SPL), stability (shown as a percentage), and the number of stimulus repetitions (illustrated as 260) over the span of the OAE measurement.

FIG. 14B is a data segment directed to noise evaluation data. As shown, this segment describes the average noise level in the testing environment (average level in dB SPL, the number ("Quiet N") of the testing stimuli presented to the ear, the number of testing stimuli which were presented when the noise level was lower or higher than a desired noise threshold level ("N"), and the percentage of the testing signals presented during low noise periods. The noise segment can also include data corresponding to peak noise at the patient end or line disruptions/power variation or noise introduced or detected during data transfer from the local to expert site. Of course, the noise segment can be combined, altered, or eliminated from the web page, or may be a pull down page which can be easily accessed as desired (such as when an inordinate number of signals occurred with an undesired noise level).

FIG. 14C illustrates a response segment that provides data in a graphic format corresponding to the response of the patient. The upper graph in FIG. 14C is a temporal waveform of the TEOAE's measured in the external ear canal (measured in pressure units of Pa) (as shown, there are two separate waveforms monitored) over a time span of about 0-20 ms. The lower graph is representative of the response spectrum (measured in dB over a frequency range of interest). The noise floor (shaded region) can also be included in this data representation (the noise corresponding to that concurrently detected during the testing procedure). This segment can also include how the TEOAE response may be correlated characterized as data over frequency ranges of interest (as SNR (signal to noise ratio)) in dB at discrete frequencies of interest (shown as 1 kHz, 2 kHz, 3 kHz, 4 kHz, and 5 kHz). As known to those of skill in the art, the correlation may be a quantified as a correlation in percent (reproducibility) between the two (or more) different waveforms and/or as the ratio or difference between the amplitude of the TEOAE versus noise within certain frequency bands or regions (shown as octave frequency bands).

Figure 15:
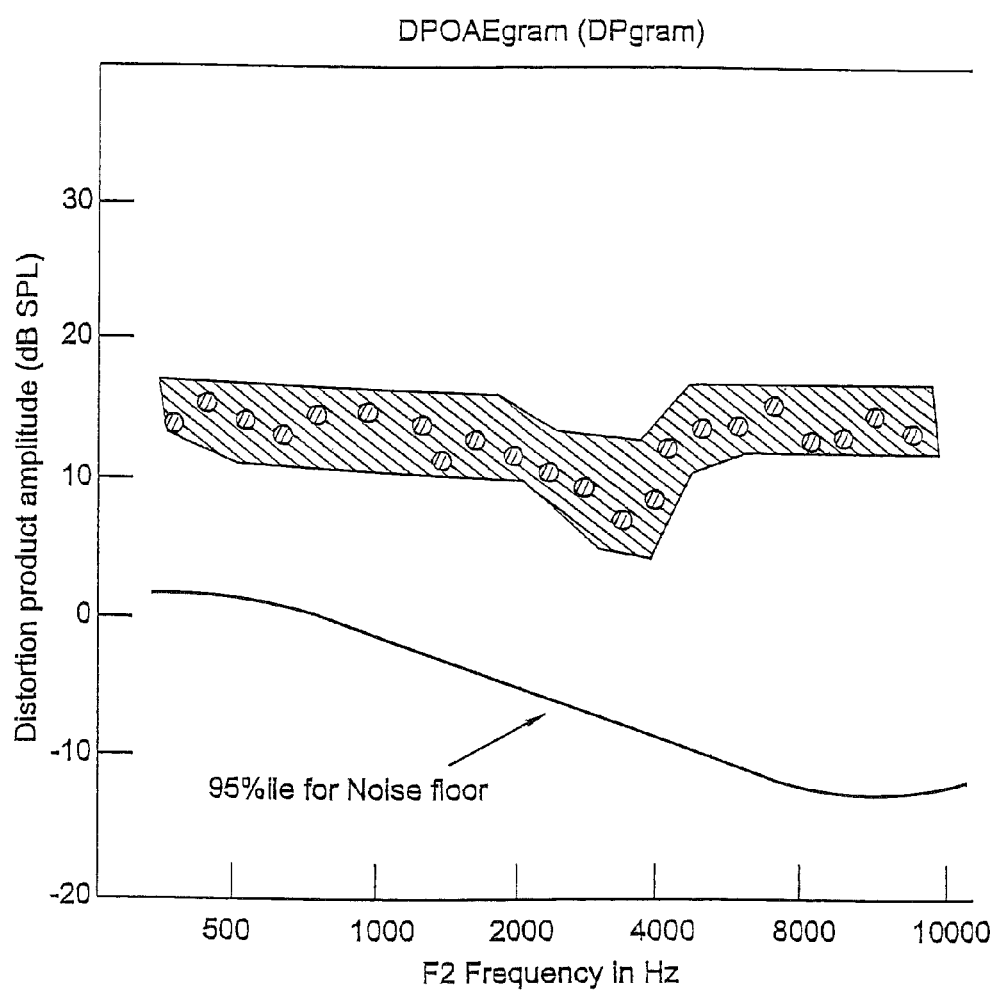
FIG. 15 illustrates examples of data that can be generated at the web page or expert site for a distortion product otoacoustic emission analysis according to embodiments of the present invention.

FIG. 15 is a graph of distortion product (DP) amplitude (dB SPL) over a stimulus frequency range of interest (shown as $f_2$ frequency over about a 500-10,000 Hz). This type of format can be described as a "Dpgram". During the evaluation, the number of stimulus, frequencies per octave and the number of octaves in the test may be manipulated by the expert site. In the example shown, a diagnostic evaluation using DPOAE's for four frequencies per octave over a range of about 500-10,000 Hz). The enclosed region in the graph corresponds to a "normal" range for DPOAE amplitudes in a desired population (such as infant, pediatric, adolescents, adult, or senior populations). The points (shown as shaded circles) drawn proximate the enclosed region corresponds to the DPOAE amplitude of the patient being tested. The DPgram can include a line corresponding to an upper limit for noise within the ear canal of a corresponding population segment (in substantially the same testing environment). As shown, the upper limit is set at the $95^{th}$ percentile of an adult population). The results shown in this figure are deemed normal. For more information on otoacoustic tests, see James W. Hall, *Handbook of Otoacoustic Emissions*, (Singular Publishing 2000); Frederick N. Martin, *Introduction to Audiology, A study Guide*, (Prentice-Hall, 1991), the contents of which are hereby incorporated by reference as if recited in full herein.

In a preferred embodiment, the system is configured to allow the measurement, screening and diagnostic assessment via a computer network to include the Internet so that the assessment can be performed at the remote (expert site) 10. The systems will transmit testing signals which can be in a range of between about 1-8 kHz at selected stimulus levels (such as at selected decibel levels within about a 60 dB range). The system then detects, measures, and records or transmits data corresponding to same from the local site 20 to the remote site 10, to thereby provide the distortion product emission (DPE) levels in the ear. These measures are associated with cochlear hair cell activity in the inner ear. These measures can be very effective in the diagnosis and screening of hearing loss categories. In certain embodiments, the system can present two primary tones at the ear canal. The cochlea produces a response to these stimuli, which is received by a microphone in the probe assembly. This signal is detected and relayed via the computer network (preferably via a web server) to the remote computer for analysis and possible modification of the test procedure as discussed above. See U.S. Pat. No. 5,885,225 to Keefe et al. and U.S. Pat. No. 5,664,577 to Lonsbury-Martin et al., for a description of testing protocols, signals, and systems, and/or ear probes, the contents of which are hereby incorporated by reference as if recited in full herein.

Figure 16:
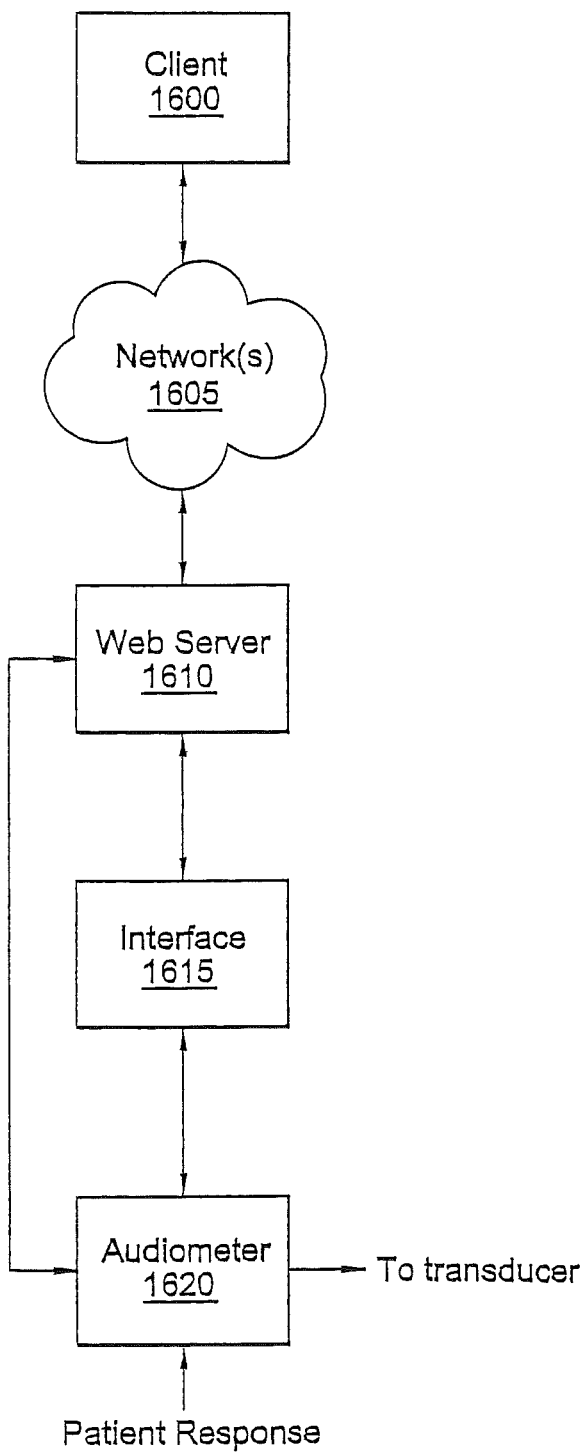
FIG. 16 is a block diagram illustrating of a networked test system according to further embodiments of the present invention.

FIG. 16 illustrates further embodiments of the present invention that may use a conventional audiometer configured to interface with a web server. As seen in FIG. 16, a client 1600 communicates with a web server 1610 over a network and/or networks 1605. The client 1600 may be a conventional web client configured as described herein and may include, for example, a networked computer, such as a desktop computer, a mobile computer or the like. The network 1605 may be the Internet, an intranet, a local area network, a wide area network, a wireless network and/or a wired network. The web server 1610 may be a general purpose computer, a network appliance or the like or any data processing system capable of carrying out the operations described herein. In a particular embodiment of the present invention, the web server is based on RabbitCore or Rabbit 2000 products provided by Rabbit Semiconductor of Davis, Calif.

The web server 1610 communicates with an audiometer 1620. The web server 1610 communicates directly to the audiometer 1620 and/or communicates with the audiometer 1620 through an interface module 1615. For example, the interface module 1615 may be provided by a microcontroller, such as a PIC16C74 from Microchip Technology, Inc. of Chandler, Ariz. The web server 1610 may communicate directly with the audiometer 1620, for example, utilizing the NOAH protocol from the Hearing Instrument Manufacturers Software Association, so as to provide improved performance, for example, in instructing the audiometer 1620 to initiate a test or in obtaining status information from the audiometer. The test and/or setup parameters of the audiometer 1620 may be set through the interface 1615 as well as obtaining test results. The audiometer 1620 provides a test signal to a transducer and receives a response from the patient, for example, by pressing a button.

Figure 17:
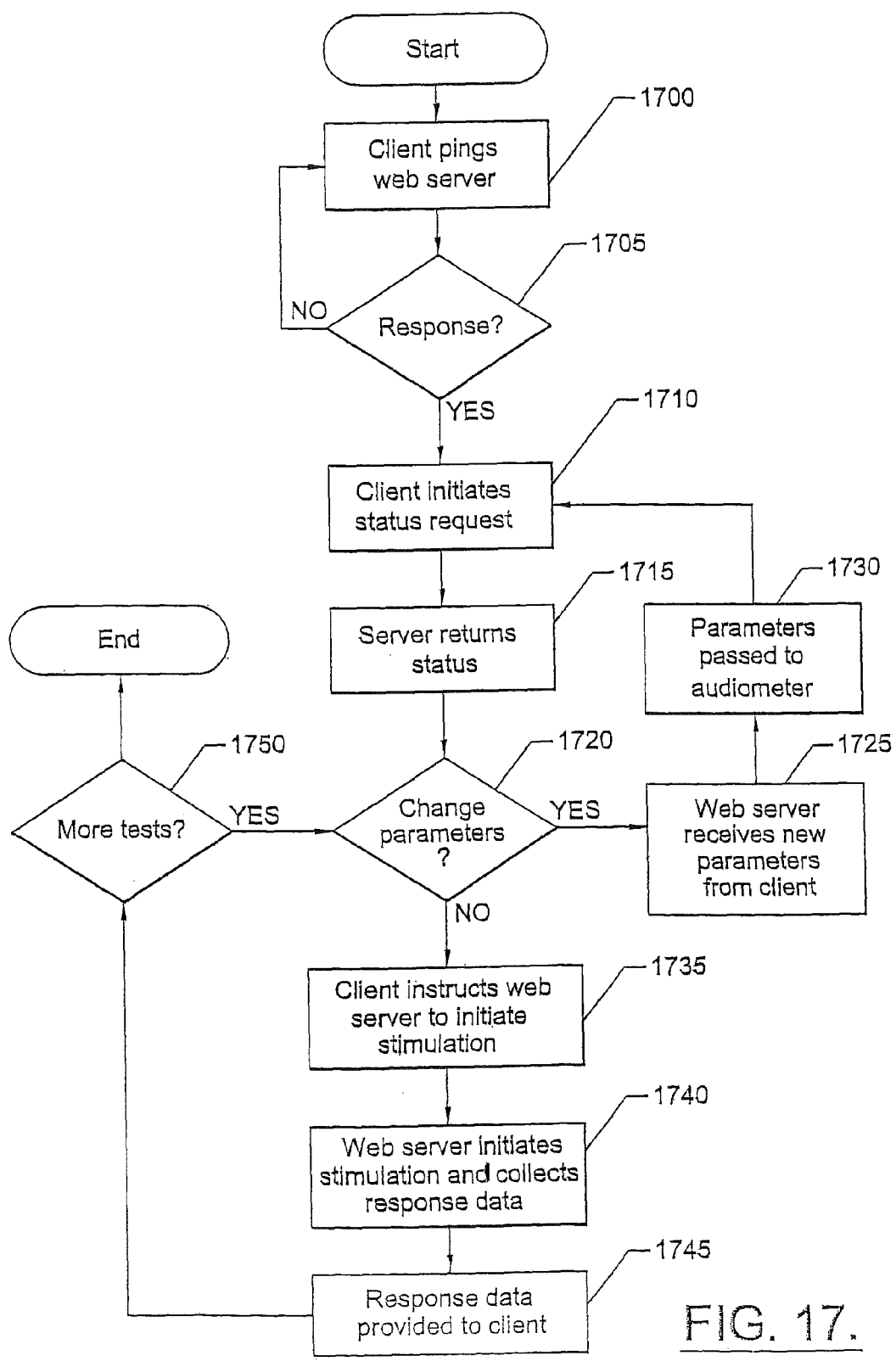
FIG. 17 is a flowchart illustrating operations of a networked test system according to further embodiments of the present invention.

FIG. 17 illustrates operations according to embodiments of the present invention. The operations illustrated in FIG. 17 may be carried out by the system of FIG. 16. As seen in FIG. 17, the client 1600 pings the web server 1610 (block 1700). If a response to the ping is not received (block 1705), operations may terminate or the ping of a same IP address or a different IP address may be performed until a response is received. If a response to the ping is received (block 1705), the client 1600 initiates a status request to the web server 1610 (block 1710). The web server 1610 collects the requested status information, for example, by requesting information from the audiometer 1620, and returns the status information to the client 1600 (block 1715). The client 1600 displays the status information for the operator and determines, for example, by receiving input from the operator, if any parameters are to be changed (block 1720).

If parameters are to be changed (block 1720), the web server 1610 receives the new parameters from the client 1600 (block 1725). The new parameters are passed to the audiometer 1620, either directly from the web server 1610 or through the interface 1615 (block 1730). The client 1600 may initiate a further status request (block 1710) to confirm that the parameters have been properly received and operations continue until no changes in the parameters are needed (block 1720).

When no parameters are to be changed (block 1720), the client 1600 instructs the web server 1610 to initiate the stimulation (block 1735). The web server 1610 initiates the stimulation by the audiometer 1620, either directly or through the interface 1615, and collects data on the patient response (block 1740), either directly or through the interface 1615. The response data is provided to the client 1600 (block 1745) for display to the operator. If more tests are to be performed (block 1750), operations may continue from block 1720.

The flowcharts, features and/or block diagrams of FIGS. 1 through 17 illustrate the architecture, functionality, and operation of possible implementations of systems, methods and computer program products for operating an auditory test and/or allocating bandwidth according to various embodiments of the present invention. In this regard, each block in the flow charts or block diagrams may represent a module, segment, or portion of code, which comprises one or more executable instructions for implementing the specified logical act(s). It should also be noted that, in some alternative implementations, the acts noted in the blocks may occur out of the order noted in the figures. For example, two blocks shown in succession may, in fact, be executed substantially concurrently, or the blocks may sometimes be executed in the reverse order, depending upon the functionality involved. Similarly, blocks may be combined such that a single module, circuit or the like provides the functionality of multiple blocks. For example, the interface 1615 of FIG. 16 could be combined with either the audiometer 1620 or the web server 1610. Similarly, the web server 1610 and the interface 1615 could all be combined into the audiometer 1620. Alternatively, if sufficient functionality is provided by the interface 1615, the direct connection from the web server 1610 to the audiometer 1620 may be eliminated. Thus, the present invention should not be construed as limited to the specific division of functions illustrated in particular embodiments of the present invention described herein.

The device 50, 50', 450, as well as the web server 1610, interface 1615 and audiometer 1620, can be configured as a portable unit which can allow a clinician at the patient site to transport the device to various sites (such as different rooms or hospital beds in the clinic environment or assisted living homes, or when visiting homes for long term or outpatient care). The hearing output device 60 or ear probe assembly 475 may be configured to be a single use disposable device, being initially sterilized for sterile testing conditions. For example, a single use, disposable (cost effective) ITE-or earplug design can be used either for a biotelemetry reading and/or for the tone output. In some embodiments, the devices may be provided on a "lending basis" and shipped out for use and returned.

Furthermore, while the present invention has been described with reference to a web server "serving" web pages to a client, as will be appreciated by those of skill in the art, alternatively, the web server may host socket connections to a client or clients and transfer data directly over such hosted socket connections. Such a direct transfer of data may be advantageous in that the overhead associated transmitting a web page in, for example, HTML may be avoided. In such a case, programs for sending and receiving data over a TCP connection may be provided at the client and the server and the data interpreted and/or displayed by an application and/or applet executing at the client.

Embodiments of the invention will be further described with reference to the following examples, the subject-matter and/or results of which is not meant to be limiting to the scope of the invention.

EXAMPLES

A pilot study was performed on 30 adult subjects (one ear per adult) to test the reliability and validity of the web-based system. This study consisted of a double-blind protocol. The investigators performed two standard pure-tone hearing threshold tests. One test was performed with a standard onsite audiometer and another test was performed with a computer web-based system of assessing hearing thresholds according to embodiments of the present invention. The participants received these tests "blind" to the examiner, as well as to which equipment was being used. The participants were placed behind a partition during the use of the standard audiometer. The participants were placed in a separate room during the use of the web-based hearing assessment. The participants received pure, tones of 250, 500, 1000, 2000, 3000, 4000, 6000, and 8000 Hz at levels of 0 to 90 dB hearing level. These are standard acoustic stimulations during hearing assessment. The participant was asked to push a button when they heard the tone. The procedures took approximately 30 minutes.

Preliminary findings indicate strong agreement between the traditional audiometric measuring equipment and the web-based system as illustrated by Table 4 below. The differences found are well within normal variations.

TABLE 4

| Mean auditory thresholds (dB) by system in thirty adult ears | | | | | | |
|---|---|---|---|---|---|---|
| Frequency (Hz) | 250 | 500 | 1000 | 2000 | 4000 | 8000 |
| Control | 19.5 | 22.0 | 12.0 | 8.5 | 8.0 | 14.0 |
| Experimental | 20.5 | 21.5 | 13.0 | 10.0 | 8.0 | 15.0 |

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, where used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed:

1. A hearing evaluation system, comprising:
a diagnostic hearing test system with a communications interface that is configured to communicate with a remote computer associated with a clinician via the Internet, wherein the diagnostic hearing test system has a function generator and attenuator, and wherein the communications interface is configured to allow a clinician using the remote computer to control the function generator during a diagnostic hearing test to select test frequencies and sound levels of sound stimuli transmitted by the device to a patient during a hearing test.

2. The system of claim 1, wherein the diagnostic hearing test system includes a housing with a processor operably associated with the function generator and attenuator and further comprises an audio analyzer in communication with the processor.

3. The system of claim 1, wherein the diagnostic hearing test system is configured to allow substantially real-time interaction between the clinician at the remote site and the patient at a test site.

4. The system of claim 1, wherein the diagnostic hearing test system is configured to allow the clinician using the remote computer to control the function generator and the attenuator and generate sound stimuli that comply with predetermined hearing test standards.

5. The system of claim 1, further comprising an output device in communication with the function generator, wherein the output device comprises a transducer for transmitting the sound stimuli to the patient, and wherein the diagnostic hearing test system includes a user input device in communication with the communications interface that allows a patient user to indicate a response to clinician-initiated test sound stimuli.

6. The system of claim 1, wherein the diagnostic hearing test system comprises a biotelemetry measurement system in communication with the communications interface, and wherein the communications interface is configured to allow the clinician to control the biotelemetry measurement system using the remote computer to evaluate otoacoustic emissions and/or middle ear pressure and compliance characteristics.

7. The system of claim 1, wherein the communications interface is configured to allow a clinician to direct the diagnostic hearing test system to transmit to a respective patient sound stimuli that includes frequency tones, narrow band noise, broadband noise, recorded noise and speech, and live speech.

8. The system of claim 1, wherein the sound stimuli is configured to have harmonic distortion of tone frequencies that meet ANSI standards.

9. The system of claim 1, wherein the diagnostic hearing test system is configured to provide visual and/or audiovisual communication between the patient and the clinician during a respective hearing test using the Internet.

10. The system of claim 1, wherein the diagnostic hearing system is configured to generate tone presentations of the sound stimuli that comply with ANSI standards.

11. The system of claim 1, further comprising a housing that holds the communications interface, the function generator and attenuator along with a web browser.

12. The system of claim 1, wherein the diagnostic hearing test system comprises a biotelemetry measurement system that is in communication with the communications interface to allow the remote computer to control the biotelemetry measurement system to obtain at least one of distortion product emission level measurements or middle ear compliance measurements of a respective patient and transmit the measurements over the Internet to the remote computer.

13. A hearing evaluation system, comprising:
a diagnostic hearing test device with a processor and a communications interface that is configured to communicate with a remote computer associated with a clinician via a computer network, wherein the diagnostic hearing test device has a function generator, attenuator and audio analyzer in communication with the processor, wherein the communications interface is configured to allow a clinician using the remote computer to control the function generator and attenuator during a diagnostic hearing test to select test frequencies and sound levels of sound stimuli that comply with predetermined testing standards to be transmitted by the hearing test device to a respective patient during a hearing test, and wherein the diagnostic hearing test device is configured to allow substantially real-time interaction between the clinician at the remote site and the patient at a test site.

14. The system of claim 13, wherein the computer network comprises the Internet, wherein the diagnostic hearing test comprises a biotelemetry measurement system in communication with the communications interface, and wherein the diagnostic hearing test device is configured to allow the clinician to control the biotelemetry measurement system using the remote computer to obtain at least one of distortion product emission level measurements or middle ear compliance measurements of a respective patient and transmit the measurements over the Internet to the remote computer.

15. The system of claim 14, wherein the communications interface is configured to allow a clinician to direct the diagnostic hearing test device to transmit sound stimuli that includes frequency tones, narrow band noise, broadband noise, recorded noise and speech, and live speech, and wherein the sound stimuli is configured to have harmonic distortion of tone frequencies that meet ANSI standards.

16. The system of claim 13, wherein the device includes or is in communication with a camera that allows the clinician at the remote site to view a patient during a respective hearing test.

17. A method of providing diagnostic hearing evaluations using the Internet, comprising:
connecting a hearing test device at a local patient site to a remote test administration site using the Internet, the hearing test device having an audiometer;
allowing a clinician to control a diagnostic hearing evaluation test administered to a patient using the Internet and the hearing test device, wherein the clinician at the remote test administration site controls hearing assessment signals generated by the hearing test device at the local patient site and monitors the patient's responses to the hearing assessment signals in substantially real time;
providing visual or audiovisual communication between the patient and the clinician during a hearing test session; and allowing the clinician at the remote test administration site to monitor noise at the patient test site during the hearing test session.

18. The method of claim 17, further comprising transmitting distortion product emission level measurements or middle ear compliance measurements over the computer network to the remote test administration site using the hearing test device.

19. The method of claim 17, wherein the hearing assessment signals have harmonic distortion of tone frequencies that meet ANSI standards.

20. The method of claim 17, wherein the hearing assessment signals include frequency tones, narrow band noise, broadband noise, recorded noise and speech, and live speech.

* * * * *

UNITED STATES PATENT AND TRADEMARK OFFICE
CERTIFICATE OF CORRECTION

PATENT NO. : 8,777,869 B2  Page 1 of 1
APPLICATION NO. : 13/610190
DATED : July 15, 2014
INVENTOR(S) : Givens et al.

It is certified that error appears in the above-identified patent and that said Letters Patent is hereby corrected as shown below:

On Title Page:
Item 60, Related U.S. Application Data:
   Please correct "Division of application No. 12/944,368,"
      to read -- Continuation of application No. 12/944,368, --

Signed and Sealed this
Thirtieth Day of December, 2014

Michelle K. Lee
*Deputy Director of the United States Patent and Trademark Office*